(12) United States Patent
Kim

(10) Patent No.: US 10,292,738 B2
(45) Date of Patent: May 21, 2019

(54) SYSTEMS AND METHODS FOR STABILIZING THE MOTION OR ADJUSTING THE POSITION OF THE SPINE

(71) Applicant: The Board of Trustees of the Leland Stanford Junior University, Palo Alto, CA (US)

(72) Inventor: Daniel H. Kim, Houston, TX (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 14/676,553

(22) Filed: Apr. 1, 2015

(65) Prior Publication Data

US 2015/0374415 A1 Dec. 31, 2015

Related U.S. Application Data

(63) Continuation of application No. 11/006,521, filed on Dec. 6, 2004, now Pat. No. 9,023,084, which is a continuation-in-part of application No. 10/970,843, filed on Oct. 20, 2004, now Pat. No. 8,167,944.

(51) Int. Cl.
| | | |
|---|---|---|
| *A61B 17/70* | (2006.01) | |
| *A61B 17/34* | (2006.01) | |
| *A61B 17/02* | (2006.01) | |
| *A61B 17/00* | (2006.01) | |

(52) U.S. Cl.
CPC ........ *A61B 17/7065* (2013.01); *A61B 17/025* (2013.01); *A61B 17/3468* (2013.01); *A61B 17/7064* (2013.01); *A61B 17/7067* (2013.01); *A61B 2017/00557* (2013.01); *A61B 2017/0256* (2013.01)

(58) Field of Classification Search
CPC ............ A61B 17/7068; A61B 17/7067; A61B 2017/564; A61B 2017/0256
See application file for complete search history.

(56) References Cited

U.S. PATENT DOCUMENTS

| | | | |
|---|---|---|---|
| 2,248,054 | A | 7/1941 | Becker |
| 2,677,369 | A | 5/1954 | Knowles |
| 3,242,120 | A | 3/1966 | Steuber |
| 3,486,505 | A | 12/1969 | Morrison |
| 3,648,691 | A | 3/1972 | Lumb et al. |
| 3,986,383 | A | 10/1976 | Petteys |
| 4,545,374 | A | 10/1985 | Jacobson |
| 4,632,101 | A | 12/1986 | Freedland |
| 4,685,447 | A | 8/1987 | Iversen et al. |

(Continued)

FOREIGN PATENT DOCUMENTS

| | | |
|---|---|---|
| CA | 268461 A | 2/1927 |
| CN | 2794456 Y | 7/2006 |

(Continued)

OTHER PUBLICATIONS

International Search Report and Written Opinion; Application No. PCT/US2005/044256; dated Jul. 28, 2006, 7 pages.

(Continued)

*Primary Examiner* — Ellen C Hammond
(74) *Attorney, Agent, or Firm* — Perkins Coie LLP

(57) ABSTRACT

The present invention provides systems and methods for stabilizing or adjusting the position of at least one spinal motion segment.

16 Claims, 29 Drawing Sheets

(56) References Cited

U.S. PATENT DOCUMENTS

| | | | |
|---|---|---|---|
| 4,799,484 A | 1/1989 | Smith et al. |
| 4,863,476 A | 9/1989 | Shepperd |
| 4,895,564 A | 1/1990 | Farrell |
| 4,986,831 A | 1/1991 | King et al. |
| 5,011,484 A | 4/1991 | Breard et al. |
| 5,015,247 A | 5/1991 | Michelson |
| 5,019,081 A | 5/1991 | Watanabe |
| 5,040,542 A | 8/1991 | Gray |
| 5,059,193 A | 10/1991 | Kuslich |
| 5,092,866 A | 3/1992 | Breard et al. |
| 5,178,628 A | 1/1993 | Otsuka et al. |
| 5,180,393 A | 1/1993 | Commarmond et al. |
| 5,182,281 A | 1/1993 | Frigola-Constansa et al. |
| 5,188,281 A | 2/1993 | Fujiwara et al. |
| 5,192,281 A | 3/1993 | de la Caffiniere |
| 5,195,526 A | 3/1993 | Michelson |
| 5,298,253 A | 3/1994 | LeFiles et al. |
| 5,368,594 A | 11/1994 | Martin et al. |
| 5,390,683 A | 2/1995 | Pisharodi |
| 5,415,661 A | 5/1995 | Holmes |
| 5,456,722 A | 10/1995 | McLeod et al. |
| 5,462,738 A | 10/1995 | LeFiles et al. |
| 5,472,452 A | 12/1995 | Trott |
| 5,487,739 A | 1/1996 | Aebischer et al. |
| 5,489,308 A | 2/1996 | Kuslich et al. |
| 5,496,318 A | 3/1996 | Howland et al. |
| 5,531,748 A | 7/1996 | de la Caffiniere et al. |
| 5,549,679 A | 8/1996 | Kuslich |
| 5,571,189 A | 11/1996 | Kuslich |
| 5,591,165 A | 1/1997 | Jackson |
| 5,609,634 A | 3/1997 | Voydeville et al. |
| 5,609,636 A | 3/1997 | Kohrs et al. |
| 5,645,599 A | 7/1997 | Samani et al. |
| 5,654,599 A | 8/1997 | Casper |
| 5,658,337 A | 8/1997 | Kohrs et al. |
| 5,674,295 A | 10/1997 | Ray et al. |
| 5,700,264 A | 12/1997 | Zucherman et al. |
| 5,725,582 A | 3/1998 | Bevan et al. |
| 5,741,253 A | 4/1998 | Michelson |
| 5,746,720 A | 5/1998 | Stouder, Jr. |
| 5,762,629 A | 6/1998 | Kambin |
| 5,836,948 A | 11/1998 | Zucherman et al. |
| 5,860,977 A | 1/1999 | Zucherman et al. |
| 5,863,948 A | 1/1999 | Epstein et al. |
| 5,876,404 A | 3/1999 | Zucherman et al. |
| RE36,211 E | 5/1999 | Nonomura et al. |
| 5,904,636 A | 5/1999 | Chen et al. |
| 5,904,686 A | 5/1999 | Zucherman et al. |
| 5,928,207 A | 7/1999 | Pisano et al. |
| 5,948,017 A | 9/1999 | Taheri |
| 5,972,015 A | 10/1999 | Scribner et al. |
| 6,039,761 A | 3/2000 | Li et al. |
| 6,045,552 A | 4/2000 | Zucherman et al. |
| 6,048,342 A * | 4/2000 | Zucherman .......... A61B 17/7062 |
| | | | 606/249 |
| 6,048,345 A | 4/2000 | Berke et al. |
| 6,066,154 A | 5/2000 | Reiley et al. |
| 6,068,630 A | 5/2000 | Zucherman et al. |
| 6,074,390 A | 6/2000 | Zucherman et al. |
| 6,080,155 A | 6/2000 | Michelson |
| 6,080,157 A | 6/2000 | Cathro et al. |
| 6,090,112 A | 7/2000 | Zucherman et al. |
| 6,096,038 A | 8/2000 | Michelson |
| 6,102,928 A | 8/2000 | Bonutti |
| D433,193 S | 10/2000 | Gaw et al. |
| 6,132,464 A | 10/2000 | Martin et al. |
| 6,149,642 A | 11/2000 | Gerhart et al. |
| 6,149,652 A | 11/2000 | Zucherman et al. |
| 6,152,926 A | 11/2000 | Zucherman et al. |
| 6,156,038 A | 12/2000 | Zucherman et al. |
| 6,159,215 A | 12/2000 | Urbahns et al. |
| 6,179,873 B1 | 1/2001 | Zientek |
| 6,183,471 B1 | 2/2001 | Zucherman et al. |
| 6,190,387 B1 | 2/2001 | Zucherman et al. |
| 6,225,048 B1 | 5/2001 | Soderberg-Naucler et al. |
| 6,235,030 B1 | 5/2001 | Zucherman et al. |
| 6,238,397 B1 | 5/2001 | Zucherman et al. |
| 6,264,651 B1 | 7/2001 | Underwood et al. |
| 6,264,656 B1 | 7/2001 | Michelson |
| 6,267,765 B1 | 7/2001 | Taylor et al. |
| 6,270,498 B1 | 8/2001 | Michelson |
| 6,280,444 B1 | 8/2001 | Zucherman et al. |
| 6,312,431 B1 | 11/2001 | Asfora |
| 6,328,730 B1 | 12/2001 | Harkrider, Jr. |
| 6,332,882 B1 | 12/2001 | Zucherman et al. |
| 6,332,883 B1 | 12/2001 | Zucherman et al. |
| 6,336,930 B1 | 1/2002 | Stalcup et al. |
| 6,348,053 B1 | 2/2002 | Cachia |
| 6,364,883 B1 | 4/2002 | Santilli |
| 6,371,989 B1 | 4/2002 | Chauvin et al. |
| 6,375,682 B1 | 4/2002 | Fleischmann et al. |
| 6,379,355 B1 | 4/2002 | Zucherman et al. |
| 6,387,130 B1 | 5/2002 | Stone et al. |
| 6,395,032 B1 | 5/2002 | Gauchet et al. |
| 6,402,740 B1 | 6/2002 | Ellis et al. |
| 6,402,750 B1 | 6/2002 | Atkinson et al. |
| 6,402,784 B1 | 6/2002 | Wardlaw et al. |
| 6,413,228 B1 | 7/2002 | Hung et al. |
| 6,419,676 B1 | 7/2002 | Zucherman et al. |
| 6,419,677 B2 | 7/2002 | Zucherman et al. |
| 6,440,169 B1 | 8/2002 | Elberg et al. |
| 6,443,988 B2 | 9/2002 | Felt et al. |
| 6,447,547 B1 | 9/2002 | Michelson |
| 6,451,019 B1 | 9/2002 | Zucherman et al. |
| 6,451,020 B1 | 9/2002 | Zucherman et al. |
| 6,464,682 B1 | 10/2002 | Snoke |
| 6,471,976 B1 | 10/2002 | Taylor et al. |
| 6,478,796 B2 | 11/2002 | Zucherman et al. |
| 6,478,822 B1 | 11/2002 | Leroux et al. |
| 6,500,178 B2 | 12/2002 | Zucherman et al. |
| 6,514,256 B2 | 2/2003 | Zucherman et al. |
| 6,530,925 B2 | 3/2003 | Boudard et al. |
| 6,558,333 B2 | 5/2003 | Gilboa et al. |
| 6,565,570 B2 | 5/2003 | Sterett et al. |
| 6,572,617 B1 | 6/2003 | Senegas et al. |
| 6,575,981 B1 | 6/2003 | Boyd et al. |
| 6,579,281 B2 | 6/2003 | Palmer et al. |
| 6,579,319 B2 | 6/2003 | Goble et al. |
| 6,582,433 B2 | 6/2003 | Yun |
| 6,582,451 B1 | 6/2003 | Marucci et al. |
| 6,599,292 B1 | 7/2003 | Ray |
| 6,602,248 B1 | 8/2003 | Sharps et al. |
| 6,610,065 B1 | 8/2003 | Branch et al. |
| 6,610,091 B1 | 8/2003 | Reiley |
| 6,616,673 B1 * | 9/2003 | Stone .................. A61B 17/025 |
| | | | 606/105 |
| 6,626,944 B1 | 9/2003 | Taylor et al. |
| 6,645,207 B2 | 11/2003 | Dixon et al. |
| 6,645,211 B2 | 11/2003 | Magana |
| 6,652,527 B2 | 11/2003 | Zucherman et al. |
| 6,652,534 B2 | 11/2003 | Zucherman et al. |
| 6,663,637 B2 | 12/2003 | Dixon et al. |
| 6,679,886 B2 | 1/2004 | Weikel et al. |
| 6,695,842 B2 | 2/2004 | Zucherman et al. |
| 6,699,246 B2 | 3/2004 | Zucherman et al. |
| 6,699,247 B2 | 3/2004 | Zucherman et al. |
| 6,702,847 B2 | 3/2004 | DiCarlo |
| 6,712,819 B2 | 3/2004 | Zucherman et al. |
| 6,716,245 B2 | 4/2004 | Pasquet et al. |
| 6,726,690 B2 | 4/2004 | Eckman |
| 6,733,534 B2 * | 5/2004 | Sherman ............ A61B 17/7065 |
| | | | 606/249 |
| 6,746,485 B1 | 6/2004 | Zucherman et al. |
| 6,761,720 B1 | 7/2004 | Senegas et al. |
| 6,783,529 B2 | 8/2004 | Hover et al. |
| 6,783,546 B2 | 8/2004 | Zucherman et al. |
| 6,796,983 B1 | 9/2004 | Zucherman et al. |
| 6,805,697 B1 | 10/2004 | Helm et al. |
| 6,835,205 B2 | 12/2004 | Atkinson et al. |
| 6,840,944 B2 | 1/2005 | Suddaby |
| 6,858,029 B2 | 2/2005 | Yeh |
| 6,869,398 B2 | 3/2005 | Obenchain et al. |
| 6,875,212 B2 | 4/2005 | Shaolian et al. |
| 6,902,566 B2 | 6/2005 | Zucherman et al. |

(56) References Cited

U.S. PATENT DOCUMENTS

| | | | |
|---|---|---|---|
| 6,926,728 B2 | 8/2005 | Zucherman et al. |
| 6,946,000 B2 | 9/2005 | Senegas et al. |
| 6,949,123 B2 | 9/2005 | Reiley |
| 6,966,930 B2 | 11/2005 | Arnin et al. |
| 6,974,478 B2 | 12/2005 | Reiley et al. |
| 7,011,685 B2 | 3/2006 | Arnin et al. |
| 7,029,473 B2 | 4/2006 | Zucherman et al. |
| 7,033,358 B2 | 4/2006 | Taylor et al. |
| 7,048,736 B2 | 5/2006 | Robinson et al. |
| 7,070,598 B2 | 7/2006 | Lim et al. |
| 7,083,649 B2 | 8/2006 | Zucherman et al. |
| 7,087,055 B2 | 8/2006 | Lim et al. |
| 7,087,083 B2 | 8/2006 | Pasquet et al. |
| 7,097,648 B1 | 8/2006 | Globerman et al. |
| 7,101,375 B2 | 9/2006 | Zucherman et al. |
| 7,163,558 B2 | 1/2007 | Senegas et al. |
| 7,179,225 B2 | 2/2007 | Shluzas et al. |
| 7,187,064 B2 | 3/2007 | Tzu et al. |
| 7,189,234 B2 | 3/2007 | Zucherman et al. |
| 7,189,236 B2 | 3/2007 | Taylor et al. |
| 7,201,751 B2 * | 4/2007 | Zucherman ............ A61K 31/37 606/249 |
| 7,217,291 B2 | 5/2007 | Zucherman et al. |
| 7,223,289 B2 | 5/2007 | Trieu et al. |
| 7,229,441 B2 | 6/2007 | Trieu et al. |
| 7,238,204 B2 | 7/2007 | Le Couedic et al. |
| 7,252,673 B2 | 8/2007 | Lim |
| 7,273,496 B2 | 9/2007 | Mitchell |
| 7,282,063 B2 | 10/2007 | Cohen et al. |
| 7,297,162 B2 | 11/2007 | Mujwid |
| 7,306,628 B2 | 12/2007 | Zucherman et al. |
| 7,318,839 B2 | 1/2008 | Malberg et al. |
| 7,320,707 B2 | 1/2008 | Zucherman et al. |
| 7,335,200 B2 | 2/2008 | Carli |
| 7,335,203 B2 | 2/2008 | Winslow et al. |
| 7,354,453 B2 | 4/2008 | McAfee |
| 7,384,340 B2 | 6/2008 | Eguchi et al. |
| 7,390,330 B2 | 6/2008 | Harp |
| 7,410,501 B2 | 8/2008 | Michelson |
| 7,442,208 B2 | 10/2008 | Mathieu et al. |
| 7,445,637 B2 | 11/2008 | Taylor |
| 7,473,268 B2 | 1/2009 | Zucherman et al. |
| 7,476,251 B2 | 1/2009 | Zucherman et al. |
| 7,481,839 B2 | 1/2009 | Zucherman et al. |
| 7,481,840 B2 | 1/2009 | Zucherman et al. |
| 7,491,204 B2 | 2/2009 | Marnay et al. |
| 7,497,859 B2 | 3/2009 | Zucherman et al. |
| 7,503,935 B2 | 3/2009 | Zucherman et al. |
| 7,504,798 B2 | 3/2009 | Kawada et al. |
| 7,510,567 B2 | 3/2009 | Zucherman et al. |
| 7,520,887 B2 | 4/2009 | Maxy et al. |
| 7,520,899 B2 | 4/2009 | Zucherman et al. |
| 7,547,308 B2 | 6/2009 | Bertagnoli et al. |
| 7,549,999 B2 | 6/2009 | Zucherman et al. |
| 7,550,009 B2 | 6/2009 | Arnin et al. |
| 7,565,259 B2 | 7/2009 | Sheng et al. |
| 7,572,276 B2 | 8/2009 | Lim et al. |
| 7,575,600 B2 | 8/2009 | Zucherman et al. |
| 7,585,313 B2 | 9/2009 | Kwak et al. |
| 7,585,316 B2 | 9/2009 | Trieu |
| 7,588,588 B2 | 9/2009 | Spitler et al. |
| 7,591,851 B2 | 9/2009 | Winslow et al. |
| 7,601,170 B2 | 10/2009 | Winslow et al. |
| 7,621,939 B2 | 11/2009 | Zucherman et al. |
| 7,635,377 B2 | 12/2009 | Zucherman et al. |
| 7,635,378 B2 | 12/2009 | Zucherman et al. |
| 7,637,950 B2 | 12/2009 | Baccelli et al. |
| 7,658,752 B2 | 2/2010 | Labrom et al. |
| 7,662,187 B2 | 2/2010 | Zucherman et al. |
| 7,666,186 B2 | 2/2010 | Harp |
| 7,666,209 B2 | 2/2010 | Zucherman et al. |
| 7,666,228 B2 | 2/2010 | Le Couedic et al. |
| 7,670,377 B2 | 3/2010 | Zucherman et al. |
| 7,682,376 B2 | 3/2010 | Trieu |
| 7,691,146 B2 | 4/2010 | Zucherman et al. |
| 7,695,513 B2 | 4/2010 | Zucherman et al. |
| 7,699,852 B2 | 4/2010 | Frankel et al. |
| 7,699,873 B2 | 4/2010 | Stevenson et al. |
| D618,796 S | 6/2010 | Cantu et al. |
| 7,727,233 B2 | 6/2010 | Blackwell et al. |
| 7,727,241 B2 | 6/2010 | Gorensek et al. |
| 7,731,751 B2 | 6/2010 | Butler et al. |
| 7,742,795 B2 | 6/2010 | Stone et al. |
| 7,749,252 B2 | 7/2010 | Zucherman et al. |
| 7,749,253 B2 | 7/2010 | Zucherman et al. |
| 7,753,938 B2 | 7/2010 | Aschmann et al. |
| 7,758,619 B2 | 7/2010 | Zucherman et al. |
| 7,758,647 B2 | 7/2010 | Arnin et al. |
| 7,763,028 B2 | 7/2010 | Lim et al. |
| 7,763,050 B2 | 7/2010 | Winslow et al. |
| 7,763,051 B2 | 7/2010 | Labrom et al. |
| 7,763,073 B2 | 7/2010 | Hawkins et al. |
| 7,763,074 B2 | 7/2010 | Altarac et al. |
| 7,766,967 B2 | 8/2010 | Francis |
| 7,776,090 B2 | 8/2010 | Winslow et al. |
| 7,780,709 B2 | 8/2010 | Bruneau et al. |
| 7,789,898 B2 | 9/2010 | Peterman |
| 7,794,476 B2 | 9/2010 | Wisnewski |
| 7,803,190 B2 | 9/2010 | Zucherman et al. |
| 7,806,911 B2 | 10/2010 | Peckham |
| 7,811,308 B2 | 10/2010 | Arnin et al. |
| 7,811,322 B2 | 10/2010 | Arnin et al. |
| 7,811,323 B2 | 10/2010 | Arnin et al. |
| 7,811,324 B2 | 10/2010 | Arnin et al. |
| 7,811,330 B2 | 10/2010 | Arnin et al. |
| 7,819,921 B2 | 10/2010 | Grotz |
| 7,828,822 B2 | 11/2010 | Zucherman et al. |
| 7,828,849 B2 | 11/2010 | Lim |
| 7,833,272 B2 | 11/2010 | Arnin et al. |
| 7,837,687 B2 | 11/2010 | Harp |
| 7,837,688 B2 | 11/2010 | Boyer, II et al. |
| 7,837,700 B2 | 11/2010 | Harp |
| 7,837,711 B2 | 11/2010 | Bruneau et al. |
| 7,837,734 B2 | 11/2010 | Zucherman et al. |
| 7,846,183 B2 | 12/2010 | Blain |
| 7,846,185 B2 | 12/2010 | Carls et al. |
| 7,846,186 B2 | 12/2010 | Taylor |
| 7,857,815 B2 | 12/2010 | Zucherman et al. |
| 7,862,569 B2 | 1/2011 | Zucherman et al. |
| 7,862,586 B2 | 1/2011 | Malek |
| 7,862,590 B2 | 1/2011 | Lim et al. |
| 7,862,592 B2 | 1/2011 | Peterson et al. |
| 7,862,615 B2 | 1/2011 | Carli et al. |
| 7,867,276 B2 | 1/2011 | Matge et al. |
| 7,871,426 B2 | 1/2011 | Chin et al. |
| 7,896,879 B2 | 3/2011 | Solsberg et al. |
| 7,942,830 B2 | 5/2011 | Solsberg et al. |
| 7,955,392 B2 | 6/2011 | Dewey et al. |
| 8,012,207 B2 | 9/2011 | Kim |
| 8,025,684 B2 | 9/2011 | Garcia-Bengochea et al. |
| 8,057,513 B2 | 11/2011 | Kohm et al. |
| 8,062,332 B2 | 11/2011 | Cunningham et al. |
| 8,100,823 B2 | 1/2012 | Harp |
| 8,123,782 B2 | 2/2012 | Altarac et al. |
| 8,123,807 B2 | 2/2012 | Kim |
| 8,128,662 B2 | 3/2012 | Altarac et al. |
| 8,152,837 B2 | 4/2012 | Altarac et al. |
| 8,167,944 B2 | 5/2012 | Kim |
| 8,226,690 B2 | 7/2012 | Altarac et al. |
| 8,273,108 B2 | 9/2012 | Altarac et al. |
| 8,277,488 B2 | 10/2012 | Altarac et al. |
| 8,292,922 B2 | 10/2012 | Altarac et al. |
| 8,317,864 B2 | 11/2012 | Kim |
| 8,409,282 B2 | 4/2013 | Kim |
| 8,425,559 B2 | 4/2013 | Tebbe et al. |
| 8,608,762 B2 | 12/2013 | Solsberg et al. |
| 8,613,747 B2 | 12/2013 | Altarac et al. |
| 8,628,574 B2 | 1/2014 | Altarac et al. |
| 8,696,671 B2 | 4/2014 | Solsberg et al. |
| 8,734,477 B2 | 5/2014 | Solsberg et al. |
| 8,740,948 B2 | 6/2014 | Reglos et al. |
| 8,845,726 B2 | 9/2014 | Tebbe et al. |
| 8,864,828 B2 | 10/2014 | Altarac et al. |
| 8,882,772 B2 | 11/2014 | Solsberg et al. |

(56) References Cited

U.S. PATENT DOCUMENTS

| | | |
|---|---|---|
| 8,894,653 B2 | 11/2014 | Solsberg et al. |
| 8,900,271 B2 | 12/2014 | Kim |
| 8,945,183 B2 | 2/2015 | Altarac et al. |
| 9,023,084 B2 | 5/2015 | Kim |
| 9,039,742 B2 | 5/2015 | Altarac et al. |
| 9,119,680 B2 | 9/2015 | Altarac et al. |
| 9,125,692 B2 | 9/2015 | Kim |
| 9,155,570 B2 | 10/2015 | Altarac et al. |
| 9,155,572 B2 | 10/2015 | Altarac et al. |
| 9,161,783 B2 | 10/2015 | Altarac et al. |
| 9,186,186 B2 | 11/2015 | Reglos et al. |
| 9,211,146 B2 | 12/2015 | Kim |
| 9,283,005 B2 | 3/2016 | Tebbe et al. |
| 9,314,279 B2 | 4/2016 | Kim |
| 9,393,055 B2 | 7/2016 | Altarac et al. |
| 2001/0012938 A1* | 8/2001 | Zucherman ........ A61B 17/7065 606/249 |
| 2001/0031965 A1 | 10/2001 | Zucherman et al. |
| 2002/0022856 A1* | 2/2002 | Johnson ......... A61B 17/320016 606/185 |
| 2002/0029039 A1* | 3/2002 | Zucherman ........ A61B 17/7065 606/249 |
| 2002/0042607 A1 | 4/2002 | Palmer et al. |
| 2002/0143331 A1 | 10/2002 | Zucherman et al. |
| 2003/0040746 A1 | 2/2003 | Mitchell et al. |
| 2003/0040753 A1 | 2/2003 | Daum et al. |
| 2003/0074075 A1 | 4/2003 | Thomas et al. |
| 2003/0149438 A1 | 8/2003 | Nichols et al. |
| 2003/0153976 A1 | 8/2003 | Cauthen et al. |
| 2003/0176921 A1 | 9/2003 | Lawson |
| 2003/0220643 A1 | 11/2003 | Ferree |
| 2003/0220650 A1 | 11/2003 | Major et al. |
| 2003/0233098 A1 | 12/2003 | Markworth |
| 2004/0087947 A1 | 5/2004 | Lim et al. |
| 2004/0106997 A1* | 6/2004 | Lieberson .......... A61B 17/1757 623/17.16 |
| 2004/0106999 A1* | 6/2004 | Mathews ............. A61B 17/025 623/17.16 |
| 2004/0167625 A1 | 8/2004 | Beyar et al. |
| 2004/0220568 A1 | 11/2004 | Zucherman et al. |
| 2005/0049708 A1 | 3/2005 | Atkinson et al. |
| 2005/0075634 A1 | 4/2005 | Zucherman et al. |
| 2005/0090822 A1* | 4/2005 | DiPoto ............. A61B 17/32002 606/86 A |
| 2005/0101955 A1 | 5/2005 | Zucherman et al. |
| 2005/0125066 A1 | 6/2005 | McAfee |
| 2005/0143738 A1 | 6/2005 | Zucherman et al. |
| 2005/0165398 A1 | 7/2005 | Reiley |
| 2005/0192586 A1 | 9/2005 | Zucherman et al. |
| 2005/0192671 A1 | 9/2005 | Bao et al. |
| 2005/0209603 A1 | 9/2005 | Zucherman et al. |
| 2005/0216087 A1 | 9/2005 | Zucherman et al. |
| 2005/0228383 A1 | 10/2005 | Zucherman et al. |
| 2005/0228384 A1 | 10/2005 | Zucherman et al. |
| 2005/0228426 A1 | 10/2005 | Campbell |
| 2005/0245937 A1 | 11/2005 | Winslow |
| 2005/0261768 A1 | 11/2005 | Trieu |
| 2005/0278036 A1 | 12/2005 | Leonard et al. |
| 2006/0036258 A1 | 2/2006 | Zucherman et al. |
| 2006/0064165 A1 | 3/2006 | Zucherman et al. |
| 2006/0064166 A1 | 3/2006 | Zucherman et al. |
| 2006/0074431 A1 | 4/2006 | Sutton et al. |
| 2006/0084976 A1 | 4/2006 | Borgstrom et al. |
| 2006/0084983 A1 | 4/2006 | Kim |
| 2006/0084985 A1 | 4/2006 | Kim |
| 2006/0084988 A1 | 4/2006 | Kim |
| 2006/0084991 A1 | 4/2006 | Borgstrom et al. |
| 2006/0085069 A1 | 4/2006 | Kim |
| 2006/0085070 A1 | 4/2006 | Kim |
| 2006/0085074 A1 | 4/2006 | Raiszadeh |
| 2006/0089718 A1 | 4/2006 | Zucherman et al. |
| 2006/0102269 A1 | 5/2006 | Uchida et al. |
| 2006/0122620 A1 | 6/2006 | Kim |
| 2006/0149254 A1 | 7/2006 | Lauryssen et al. |
| 2006/0149289 A1 | 7/2006 | Winslow et al. |
| 2006/0167416 A1 | 7/2006 | Mathis et al. |
| 2006/0195102 A1 | 8/2006 | Malandain |
| 2006/0217811 A1 | 9/2006 | Lambrecht et al. |
| 2006/0224159 A1 | 10/2006 | Anderson |
| 2006/0235386 A1 | 10/2006 | Anderson |
| 2006/0241597 A1 | 10/2006 | Mitchell et al. |
| 2006/0241614 A1 | 10/2006 | Bruneau et al. |
| 2006/0241757 A1 | 10/2006 | Anderson |
| 2006/0247623 A1 | 11/2006 | Anderson et al. |
| 2006/0247632 A1 | 11/2006 | Winslow et al. |
| 2006/0247633 A1 | 11/2006 | Winslow et al. |
| 2006/0247650 A1 | 11/2006 | Yerby et al. |
| 2006/0247773 A1 | 11/2006 | Stamp |
| 2006/0264938 A1 | 11/2006 | Zucherman et al. |
| 2006/0264939 A1 | 11/2006 | Zucherman et al. |
| 2006/0265066 A1 | 11/2006 | Zucherman et al. |
| 2006/0265067 A1 | 11/2006 | Zucherman et al. |
| 2006/0271044 A1 | 11/2006 | Petrini et al. |
| 2006/0271049 A1 | 11/2006 | Zucherman et al. |
| 2006/0271055 A1 | 11/2006 | Thramann |
| 2006/0271061 A1 | 11/2006 | Beyar et al. |
| 2006/0271194 A1 | 11/2006 | Zucherman et al. |
| 2006/0276801 A1 | 12/2006 | Yerby et al. |
| 2006/0276897 A1 | 12/2006 | Winslow et al. |
| 2006/0282077 A1 | 12/2006 | Labrom et al. |
| 2006/0282078 A1 | 12/2006 | Labrom et al. |
| 2007/0016196 A1 | 1/2007 | Winslow et al. |
| 2007/0055237 A1 | 3/2007 | Edidin et al. |
| 2007/0055246 A1 | 3/2007 | Zucherman et al. |
| 2007/0073289 A1 | 3/2007 | Kwak et al. |
| 2007/0100340 A1 | 5/2007 | Lange et al. |
| 2007/0100366 A1 | 5/2007 | Dziedzic et al. |
| 2007/0123863 A1 | 5/2007 | Winslow et al. |
| 2007/0123904 A1 | 5/2007 | Stad et al. |
| 2007/0161991 A1 | 7/2007 | Altarac et al. |
| 2007/0161993 A1 | 7/2007 | Lowery et al. |
| 2007/0173818 A1 | 7/2007 | Hestad et al. |
| 2007/0173821 A1 | 7/2007 | Trieu |
| 2007/0173822 A1 | 7/2007 | Bruneau et al. |
| 2007/0173823 A1 | 7/2007 | Dewey et al. |
| 2007/0173832 A1 | 7/2007 | Tebbe et al. |
| 2007/0173939 A1 | 7/2007 | Kim et al. |
| 2007/0179500 A1 | 8/2007 | Chin et al. |
| 2007/0185490 A1 | 8/2007 | Implicito |
| 2007/0191948 A1 | 8/2007 | Arnin et al. |
| 2007/0191991 A1 | 8/2007 | Addink |
| 2007/0198045 A1 | 8/2007 | Morton et al. |
| 2007/0198091 A1 | 8/2007 | Boyer et al. |
| 2007/0203493 A1 | 8/2007 | Zucherman et al. |
| 2007/0203495 A1 | 8/2007 | Zucherman et al. |
| 2007/0203496 A1 | 8/2007 | Zucherman et al. |
| 2007/0203497 A1 | 8/2007 | Zucherman et al. |
| 2007/0203501 A1 | 8/2007 | Zucherman et al. |
| 2007/0208345 A1 | 9/2007 | Marnay et al. |
| 2007/0208346 A1 | 9/2007 | Marnay et al. |
| 2007/0208366 A1 | 9/2007 | Pellegrino et al. |
| 2007/0210018 A1 | 9/2007 | Wallwiener et al. |
| 2007/0225706 A1 | 9/2007 | Clark et al. |
| 2007/0225724 A1 | 9/2007 | Edmond |
| 2007/0225807 A1 | 9/2007 | Phan et al. |
| 2007/0225814 A1 | 9/2007 | Atkinson et al. |
| 2007/0233068 A1 | 10/2007 | Bruneau et al. |
| 2007/0233074 A1 | 10/2007 | Anderson et al. |
| 2007/0233076 A1 | 10/2007 | Trieu |
| 2007/0233077 A1 | 10/2007 | Khalili |
| 2007/0233081 A1 | 10/2007 | Pasquet et al. |
| 2007/0233082 A1 | 10/2007 | Chin et al. |
| 2007/0233083 A1 | 10/2007 | Abdou |
| 2007/0233084 A1 | 10/2007 | Betz et al. |
| 2007/0233088 A1 | 10/2007 | Edmond |
| 2007/0233089 A1 | 10/2007 | DiPoto et al. |
| 2007/0233096 A1 | 10/2007 | Garcia-Bengochea |
| 2007/0233098 A1 | 10/2007 | Mastrorio et al. |
| 2007/0233129 A1 | 10/2007 | Bertagnoli et al. |
| 2007/0250060 A1 | 10/2007 | Anderson et al. |
| 2007/0260245 A1 | 11/2007 | Malandain et al. |
| 2007/0265623 A1 | 11/2007 | Malandain et al. |
| 2007/0265624 A1 | 11/2007 | Zucherman et al. |

(56) References Cited

U.S. PATENT DOCUMENTS

| | | |
|---|---|---|
| 2007/0265625 A1 | 11/2007 | Zucherman et al. |
| 2007/0265626 A1 | 11/2007 | Seme |
| 2007/0270822 A1 | 11/2007 | Heinz |
| 2007/0270823 A1 | 11/2007 | Trieu et al. |
| 2007/0270824 A1 | 11/2007 | Lim et al. |
| 2007/0270826 A1 | 11/2007 | Trieu et al. |
| 2007/0270828 A1 | 11/2007 | Bruneau et al. |
| 2007/0270829 A1 | 11/2007 | Carls et al. |
| 2007/0270834 A1 | 11/2007 | Bruneau et al. |
| 2007/0272259 A1 | 11/2007 | Allard et al. |
| 2007/0276368 A1 | 11/2007 | Trieu et al. |
| 2007/0276369 A1 | 11/2007 | Allard et al. |
| 2007/0276372 A1 | 11/2007 | Malandain et al. |
| 2007/0276373 A1 | 11/2007 | Malandain |
| 2007/0276390 A1 | 11/2007 | Solsberg et al. |
| 2007/0276493 A1* | 11/2007 | Malandain ............ A61B 17/025 623/17.11 |
| 2007/0276496 A1 | 11/2007 | Lange et al. |
| 2007/0276497 A1 | 11/2007 | Anderson |
| 2007/0276500 A1 | 11/2007 | Zucherman et al. |
| 2008/0015700 A1 | 1/2008 | Zucherman et al. |
| 2008/0021468 A1 | 1/2008 | Zucherman et al. |
| 2008/0021560 A1 | 1/2008 | Zucherman et al. |
| 2008/0021561 A1 | 1/2008 | Zucherman et al. |
| 2008/0027545 A1 | 1/2008 | Zucherman et al. |
| 2008/0027552 A1 | 1/2008 | Zucherman et al. |
| 2008/0027553 A1 | 1/2008 | Zucherman et al. |
| 2008/0033445 A1 | 2/2008 | Zucherman et al. |
| 2008/0033553 A1 | 2/2008 | Zucherman et al. |
| 2008/0033558 A1 | 2/2008 | Zucherman et al. |
| 2008/0033559 A1 | 2/2008 | Zucherman et al. |
| 2008/0039853 A1 | 2/2008 | Zucherman et al. |
| 2008/0039858 A1 | 2/2008 | Zucherman et al. |
| 2008/0039859 A1 | 2/2008 | Zucherman et al. |
| 2008/0039945 A1 | 2/2008 | Zucherman et al. |
| 2008/0039946 A1 | 2/2008 | Zucherman et al. |
| 2008/0039947 A1 | 2/2008 | Zucherman et al. |
| 2008/0045958 A1 | 2/2008 | Zucherman et al. |
| 2008/0045959 A1 | 2/2008 | Zucherman et al. |
| 2008/0046081 A1 | 2/2008 | Zucherman et al. |
| 2008/0046085 A1 | 2/2008 | Zucherman et al. |
| 2008/0046086 A1 | 2/2008 | Zucherman et al. |
| 2008/0046087 A1 | 2/2008 | Zucherman et al. |
| 2008/0046088 A1 | 2/2008 | Zucherman et al. |
| 2008/0051785 A1 | 2/2008 | Zucherman et al. |
| 2008/0051896 A1* | 2/2008 | Suddaby ............ A61B 17/7065 623/17.12 |
| 2008/0051898 A1 | 2/2008 | Zucherman et al. |
| 2008/0051899 A1 | 2/2008 | Zucherman et al. |
| 2008/0051904 A1 | 2/2008 | Zucherman et al. |
| 2008/0051905 A1 | 2/2008 | Zucherman et al. |
| 2008/0058806 A1 | 3/2008 | Klyce et al. |
| 2008/0058807 A1 | 3/2008 | Klyce et al. |
| 2008/0058808 A1 | 3/2008 | Klyce et al. |
| 2008/0058941 A1 | 3/2008 | Zucherman et al. |
| 2008/0065086 A1 | 3/2008 | Zucherman et al. |
| 2008/0065212 A1 | 3/2008 | Zucherman et al. |
| 2008/0065213 A1 | 3/2008 | Zucherman et al. |
| 2008/0065214 A1 | 3/2008 | Zucherman et al. |
| 2008/0071280 A1 | 3/2008 | Winslow |
| 2008/0071378 A1 | 3/2008 | Zucherman et al. |
| 2008/0071380 A1* | 3/2008 | Sweeney ............ A61B 17/7065 623/17.16 |
| 2008/0086212 A1 | 4/2008 | Zucherman et al. |
| 2008/0108990 A1 | 5/2008 | Mitchell et al. |
| 2008/0114455 A1 | 5/2008 | Lange et al. |
| 2008/0132952 A1 | 6/2008 | Malandain et al. |
| 2008/0167655 A1 | 7/2008 | Wang et al. |
| 2008/0167656 A1 | 7/2008 | Zucherman et al. |
| 2008/0172057 A1 | 7/2008 | Zucherman et al. |
| 2008/0177272 A1 | 7/2008 | Zucherman et al. |
| 2008/0177306 A1 | 7/2008 | Lamborne et al. |
| 2008/0177312 A1 | 7/2008 | Perez-Cruet et al. |
| 2008/0183210 A1 | 7/2008 | Zucherman et al. |
| 2008/0188895 A1 | 8/2008 | Cragg et al. |
| 2008/0208344 A1 | 8/2008 | Kilpela et al. |
| 2008/0215058 A1 | 9/2008 | Zucherman et al. |
| 2008/0221692 A1 | 9/2008 | Zucherman et al. |
| 2008/0228225 A1 | 9/2008 | Trautwein et al. |
| 2008/0234708 A1 | 9/2008 | Houser et al. |
| 2008/0234824 A1 | 9/2008 | Youssef et al. |
| 2008/0288075 A1 | 11/2008 | Zucherman et al. |
| 2008/0319550 A1 | 12/2008 | Altarac et al. |
| 2009/0012528 A1 | 1/2009 | Aschmann et al. |
| 2009/0118833 A1 | 5/2009 | Hudgins et al. |
| 2009/0125030 A1 | 5/2009 | Tebbe et al. |
| 2009/0125036 A1 | 5/2009 | Bleich |
| 2009/0138046 A1 | 5/2009 | Altarac et al. |
| 2009/0138055 A1 | 5/2009 | Altarac et al. |
| 2009/0222043 A1 | 9/2009 | Altarac et al. |
| 2009/0248079 A1 | 10/2009 | Kwak et al. |
| 2009/0292315 A1 | 11/2009 | Trieu |
| 2010/0042217 A1 | 2/2010 | Zucherman et al. |
| 2010/0082108 A1 | 4/2010 | Zucherman et al. |
| 2010/0114100 A1 | 5/2010 | Mehdizade |
| 2010/0131009 A1 | 5/2010 | Roebling et al. |
| 2010/0228092 A1 | 9/2010 | Ortiz et al. |
| 2010/0234889 A1 | 9/2010 | Hess |
| 2010/0262243 A1 | 10/2010 | Zucherman et al. |
| 2010/0280551 A1 | 11/2010 | Pool et al. |
| 2010/0305611 A1 | 12/2010 | Zucherman et al. |
| 2011/0245833 A1 | 10/2011 | Anderson |
| 2011/0313457 A1 | 12/2011 | Reglos et al. |
| 2012/0078301 A1 | 3/2012 | Hess |
| 2012/0158063 A1 | 6/2012 | Altarac et al. |
| 2012/0226315 A1 | 9/2012 | Altarac et al. |
| 2012/0232552 A1 | 9/2012 | Morgenstern Lopez et al. |
| 2012/0303039 A1 | 11/2012 | Chin et al. |
| 2012/0330359 A1 | 12/2012 | Kim |
| 2013/0012998 A1 | 1/2013 | Altarac et al. |
| 2013/0072985 A1 | 3/2013 | Kim |
| 2013/0150886 A1 | 6/2013 | Altarac et al. |
| 2013/0165974 A1 | 6/2013 | Kim |
| 2013/0165975 A1 | 6/2013 | Tebbe et al. |
| 2013/0172932 A1 | 7/2013 | Altarac et al. |
| 2013/0172933 A1 | 7/2013 | Altarac et al. |
| 2013/0289399 A1 | 10/2013 | Choi et al. |
| 2013/0289622 A1 | 10/2013 | Kim |
| 2014/0081332 A1 | 3/2014 | Altarac et al. |
| 2014/0214082 A1 | 7/2014 | Reglos et al. |
| 2014/0228884 A1 | 8/2014 | Altarac et al. |
| 2014/0275992 A1 | 9/2014 | Choi et al. |
| 2015/0150598 A1 | 6/2015 | Tebbe et al. |
| 2015/0150604 A1 | 6/2015 | Kim |
| 2015/0164560 A1 | 6/2015 | Altarac et al. |
| 2016/0030092 A1 | 2/2016 | Altarac et al. |
| 2016/0045232 A1 | 2/2016 | Altarac et al. |
| 2016/0066963 A1 | 3/2016 | Kim |
| 2016/0135853 A1 | 5/2016 | Altarac et al. |
| 2016/0248222 A1 | 8/2016 | Miyata |

FOREIGN PATENT DOCUMENTS

| | | |
|---|---|---|
| CN | 101897603 | 12/2010 |
| DE | 69507480 | 9/1999 |
| EP | 322334 | 6/1989 |
| EP | 0767636 | 4/1997 |
| EP | 0768843 B1 | 4/1997 |
| EP | 0959792 B1 | 12/1999 |
| EP | 1027004 A1 | 8/2000 |
| EP | 1030615 A1 | 8/2000 |
| EP | 1138268 | 10/2001 |
| EP | 1330987 A1 | 7/2003 |
| EP | 1056408 B1 | 12/2003 |
| EP | 1343424 B1 | 9/2004 |
| EP | 1454589 A1 | 9/2004 |
| EP | 1148850 B1 | 4/2005 |
| EP | 1570793 A2 | 9/2005 |
| EP | 1299042 B1 | 3/2006 |
| EP | 1578314 B1 | 5/2007 |
| EP | 1675535 B1 | 5/2007 |
| EP | 1861046 A2 | 12/2007 |
| FR | 2681525 A1 | 3/1993 |
| FR | 2722980 A1 | 2/1996 |

(56) References Cited

FOREIGN PATENT DOCUMENTS

| | | |
|---|---|---|
| FR | 2816197 A1 | 5/2002 |
| FR | 2884136 A1 | 10/2006 |
| FR | 2888744 A1 | 1/2007 |
| SU | 988281 A1 | 1/1983 |
| WO | WO-9404088 A1 | 3/1994 |
| WO | WO-9426192 A1 | 11/1994 |
| WO | WO-9525485 A1 | 9/1995 |
| WO | WO-9531158 A1 | 11/1995 |
| WO | WO-9600049 A1 | 1/1996 |
| WO | WO-9829047 A1 | 7/1998 |
| WO | WO-9921500 A1 | 5/1999 |
| WO | WO-9921501 A1 | 5/1999 |
| WO | WO-9942051 A1 | 8/1999 |
| WO | WO-0013619 A1 | 3/2000 |
| WO | WO-0044319 A1 | 8/2000 |
| WO | WO-0044321 A2 | 8/2000 |
| WO | WO-0128442 A1 | 4/2001 |
| WO | WO-0191657 A1 | 12/2001 |
| WO | WO-0191658 A1 | 12/2001 |
| WO | WO-0203882 A2 | 1/2002 |
| WO | WO-0207623 A1 | 1/2002 |
| WO | WO-0207624 A1 | 1/2002 |
| WO | WO-02051326 A1 | 7/2002 |
| WO | WO-02067793 A2 | 9/2002 |
| WO | WO-02071960 A1 | 9/2002 |
| WO | WO-02076336 A2 | 10/2002 |
| WO | WO-03007791 A2 | 1/2003 |
| WO | WO-03007829 A1 | 1/2003 |
| WO | WO-03008016 A2 | 1/2003 |
| WO | WO-03015646 A2 | 2/2003 |
| WO | WO-03024298 A2 | 3/2003 |
| WO | WO-03045262 A2 | 6/2003 |
| WO | WO-03099147 A1 | 12/2003 |
| WO | WO-03101350 A1 | 12/2003 |
| WO | WO-04073533 A1 | 9/2004 |
| WO | WO-04110300 A2 | 12/2004 |
| WO | WO-05009300 A1 | 2/2005 |
| WO | WO-05013839 A2 | 2/2005 |
| WO | WO-05025461 A2 | 3/2005 |
| WO | WO-05041799 A1 | 5/2005 |
| WO | WO-05044152 A1 | 5/2005 |
| WO | WO-05055868 A2 | 6/2005 |
| WO | WO-05079672 A2 | 9/2005 |
| WO | WO-2005086776 A2 | 9/2005 |
| WO | WO-05115261 A1 | 12/2005 |
| WO | WO-06033659 A2 | 3/2006 |
| WO | WO-06034423 A2 | 3/2006 |
| WO | WO-06039243 | 4/2006 |
| WO | WO-06039260 A2 | 4/2006 |
| WO | WO-06045094 A2 | 4/2006 |
| WO | WO-2006045094 A2 | 4/2006 |
| WO | WO-06063047 A2 | 6/2006 |
| WO | WO-06065774 A1 | 6/2006 |
| WO | WO-2006063047 A2 | 6/2006 |
| WO | WO-2006064356 A1 | 6/2006 |
| WO | WO-2006089085 A2 | 8/2006 |
| WO | WO-06102269 A2 | 9/2006 |
| WO | WO-06102428 A1 | 9/2006 |
| WO | WO-06102485 A2 | 9/2006 |
| WO | WO-06107539 A1 | 10/2006 |
| WO | WO-06110462 A2 | 10/2006 |
| WO | WO-06110464 A1 | 10/2006 |
| WO | WO-06110767 A1 | 10/2006 |
| WO | WO-06113080 A2 | 10/2006 |
| WO | WO-06113406 A2 | 10/2006 |
| WO | WO-06113814 A2 | 10/2006 |
| WO | WO-06118945 A1 | 11/2006 |
| WO | WO-06119235 A1 | 11/2006 |
| WO | WO-06119236 A2 | 11/2006 |
| WO | WO-06135511 A1 | 12/2006 |
| WO | WO-07015028 A1 | 2/2007 |
| WO | WO-07035120 A1 | 3/2007 |
| WO | WO-07075375 A2 | 7/2007 |
| WO | WO-07075788 A2 | 7/2007 |
| WO | WO-07075791 A2 | 7/2007 |
| WO | WO-07089605 A2 | 8/2007 |
| WO | WO-07089905 A2 | 8/2007 |
| WO | WO-07089975 A1 | 8/2007 |
| WO | WO-07097735 A2 | 8/2007 |
| WO | WO-07109402 A2 | 9/2007 |
| WO | WO-07110604 A1 | 10/2007 |
| WO | WO-07111795 A1 | 10/2007 |
| WO | WO-07111979 A2 | 10/2007 |
| WO | WO-07111999 A2 | 10/2007 |
| WO | WO-07117882 A1 | 10/2007 |
| WO | WO-07121070 A2 | 10/2007 |
| WO | WO-07127550 A2 | 11/2007 |
| WO | WO-07127588 A1 | 11/2007 |
| WO | WO-07127677 A1 | 11/2007 |
| WO | WO-07127689 A2 | 11/2007 |
| WO | WO-07127694 A2 | 11/2007 |
| WO | WO-07127734 A2 | 11/2007 |
| WO | WO-07127736 A2 | 11/2007 |
| WO | WO-07131165 A2 | 11/2007 |
| WO | WO-07134113 A2 | 11/2007 |
| WO | WO-2008009049 A1 | 1/2008 |
| WO | WO-08048645 A2 | 4/2008 |
| WO | WO-2008057506 A2 | 5/2008 |
| WO | WO-2008130564 A1 | 10/2008 |
| WO | WO-2009014728 A2 | 1/2009 |
| WO | WO-2009033093 A1 | 3/2009 |
| WO | WO-2009086010 A2 | 7/2009 |
| WO | WO-2009091922 A2 | 7/2009 |
| WO | WO-2009094463 A2 | 7/2009 |
| WO | WO-2009114479 A2 | 9/2009 |
| WO | WO-2011084477 A2 | 7/2011 |
| WO | WO-2015171814 A1 | 11/2015 |

OTHER PUBLICATIONS

International Search Report and Written Opinion; Application No. PCT/US2007/023312; dated May 22, 2008, 14 pages.

Minns, R.J., et al., "Preliminary Design and Experimental Studies of a Noval Soft Implant for Correcting Sagittal Plane Instability in the Lumbar Spine," (1997) Spine, 22(16): 1819-1827.

International Search Report and Written Opinion; Application No. PCT/US2006/048611; dated Oct. 14, 2008; 10 pages.

International Search Report and Written Opinion; Application No. PCT/US2006/048614; dated Feb. 3, 2006; 23 pages.

International Search Report and Written Opinion; Application No. PCT/US2008/004901; dated Aug. 19, 2008, 7 pages.

International Search Report and Written Opinion; Application No. PCT/US2008/008983; dated Feb. 23, 2009, 7 pages.

International Search Report and Written Opinion; Application No. PCT/US2008/075487; dated Dec. 31, 2008, 7 pages.

International Search Report and Written Opinion; Application No. PCT/US2009/036561; dated Sep. 17, 2009, 12 pages.

European Search Report Application No. EP05849654.8; Applicant: The Board of Trustees of the Leland Stanford Junior University; Date of Completion: Jun. 21, 2011, 4 pages.

International Search Report and Written Opinion; Application No. PCT/US2005/038026; dated Apr. 22, 2008, 9 pages.

International Search Report and Written Opinion; Application No. PCT/US2006/047824; dated Oct. 16, 2008, 17 pages.

International Search Report and Written Opinion; Application No. PCT/US2007/022171; dated Apr. 15, 2008, 9 pages.

International Search Report and Written Opinion; Application No. PCT/US2008/008382; dated Mar. 2, 2009, 13 pages.

International Search Report and Written Opinion; Application No. PCT/US2008/087527; dated Jul. 30, 2009, 10 pages.

International Search Report and Written Opinion; Application No. PCT/US2009/031150; dated Aug. 28, 2009, 6 pages.

Supplementary European Search Report; Application No. EP05849654.6; Applicant: Vertiflex, Inc.; Date of Completion: May 15, 2009, 10 pages.

Swan, Colby, "Preliminary Design and Experimental Studies of a Novel Soft Implant for Correcting Sogittal Plane Instability in the Lumbar Spine," Spine, 1997, 22(16), 1826-1827.

(56) References Cited

OTHER PUBLICATIONS

Supplementary European Search Report; Application No. EP05849654; Applicant: The Board of Trustees of Leland Stanford Junior University; Date of Completion: May 15, 2009, 5 pages.

International Search Report and Written Opinion; Application No. PCT/US2010/060498; dated Aug. 25, 2011, 17 pages.

International Search Report and Written Opinion; Application No. PCT/US2009/031710; dated Sep. 1, 2009, 10 pages.

International Search Report, counterpart PCT Application PCT/US2013/038534, Applicant: Vertiflex, Inc., Aug. 7, 2013, 16 pages.

McCulloch, John A., Young, Paul H., "Essentials of Spinal Microsurgery," 1998, pp. 453-485. Lippincott-Raven Publishers, Philadelphia, PA (37 pages total).

Lee, Seungcheol et al., "New Surgical Techniques of Percutaneous Endoscopic Lumbar . Disectomy for Migrated Disc Herniation," Joint Dis. Rel. Surg., 16(2); pp. 102-110 (2005).

Choi, Gun et al., "Percutaneous Endoscopic Interlaminar Disectomy for Intracanalicular Disc Herniations at L5-S1 Using a Rigid Working Channel Endoscope," Operative Neurosurg., 58: pp. 59-68 (2006).

Lee, Seungcheol et al., "Percutaneous Endoscopic Interlaminar Disectomy for L5-S1 Disc Herniation: Axillary Approach and Preliminary Results," J. of Korean Neurosurg. Soc., 40: pp. 19-83 (2006).

Vertos mild Devices Kit—PRT-00430-C—Instructions for Use (13 pages total); see http://vertosmed.com/docs/mildIFU_PRT-00430-C.pdf.

Decision on Petition in U.S. Appl. No. 60/592,099, May 4, 2005.

Vaccaro, Alexander J. et al., MasterCases Spine Surgery, 2001, pp. 100-107. Thieme Medical Publishers, Inc., NY. (10 pages total).

Tredway, Trent L. et al., "Minimally Invasive Transforaminal Lumbar Interbody Fusion (MI-TLIF) and Lateral Mass Fusion with the MetRx System," (14 pages total).

Fast, Avital et al., "Surgical Treatment of Lumbar Spinal Stenosis in the Elderly," Arch Phys. Med Rehabil., Mar. 1985, pp. 149-151, vol. 66.

Palmer, Sylvain et al., "Bilateral decompressive surgery in lumbar spinal stenosis associated with spondylolisthesis: unilateral approach and use of a microscope and tubular retractor system," Neurosurgery Focus, Jul. 2002, pp. 1-6, vol. 13.

International Search Report and Written Opinion; Application No. PCT/US2009/029537; Applicant: Vertiflex, Inc. dated Aug. 3, 2015, 14 pages.

ASNR Neuroradiology Patient Information website, Brain and Spine Imaging: A Patient's Guide to Neuroradiology; Myelography; http://www.asnr.org/patientinfo/procedures/myelography.shtml#sthash.sXIDOxWq.dpbs, Copyright 2012-2013.

European Search Report Application No. EP05815519.3; Applicant: The Board of Trustees of the Leland Stanford Junior University; dated Mar. 2, 2016, 4 pages.

* cited by examiner

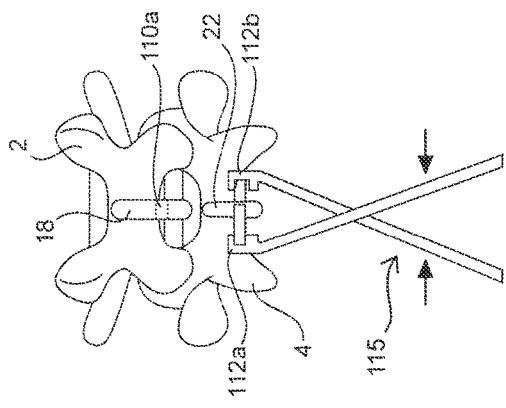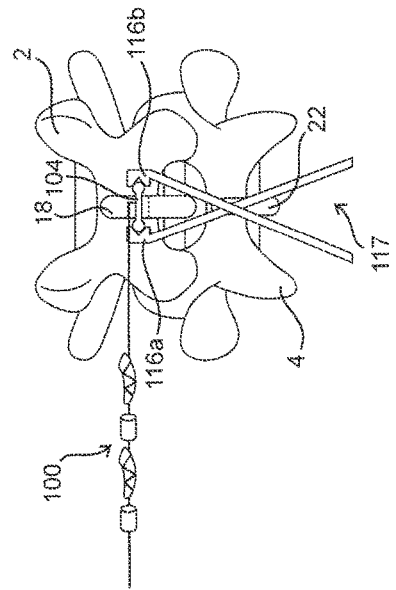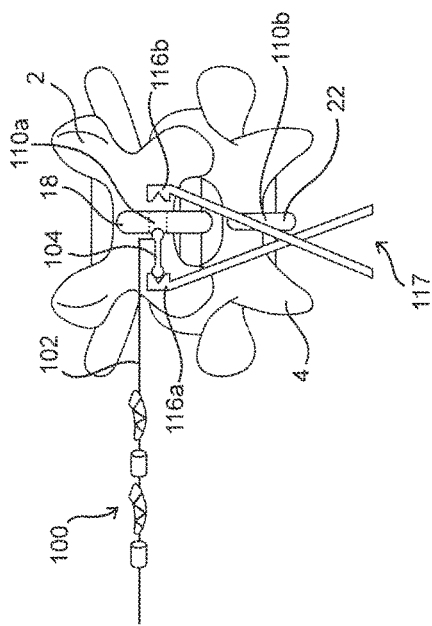

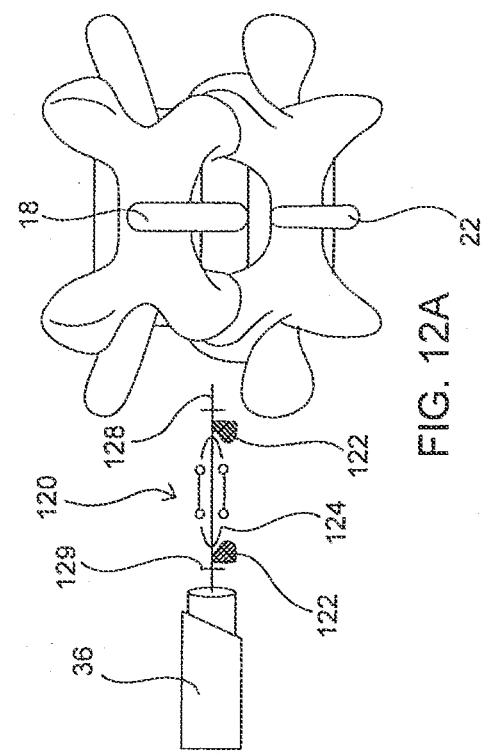
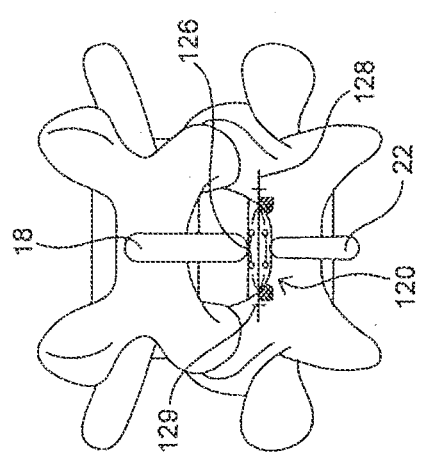
FIG. 12A
FIG. 12B
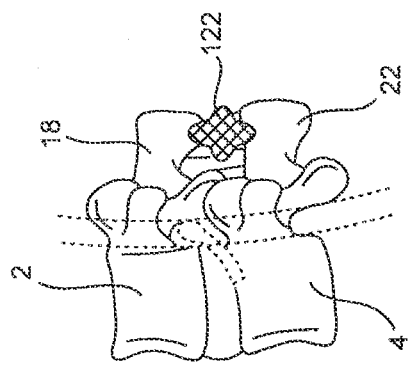
FIG. 12C
FIG. 12D
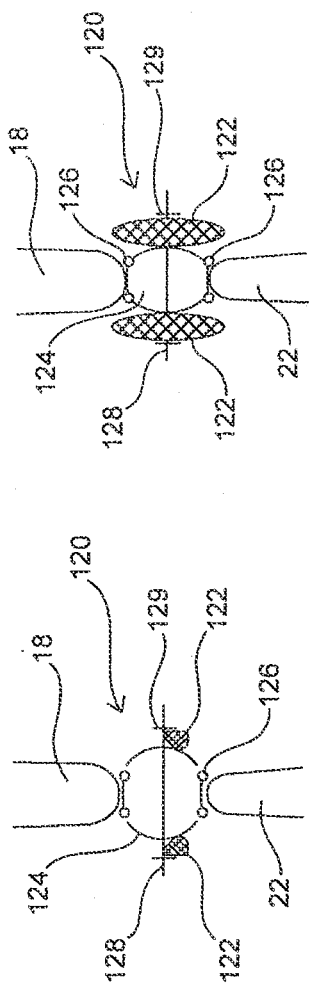
FIG. 12E

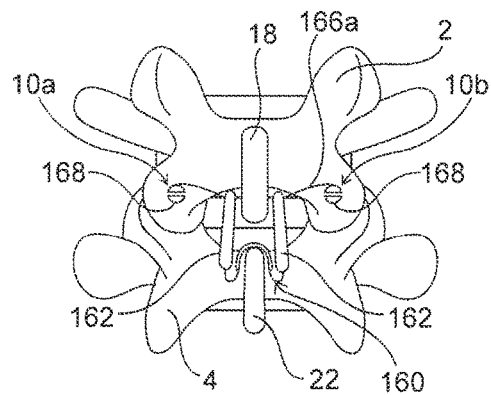 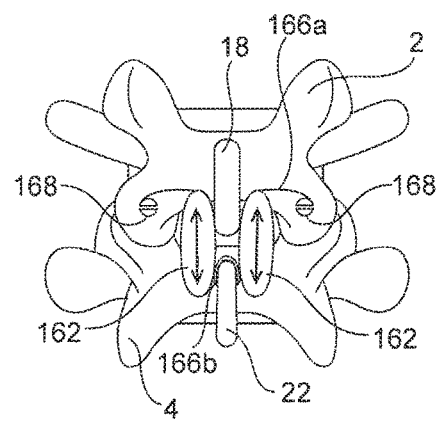
FIG. 16A  FIG. 16B
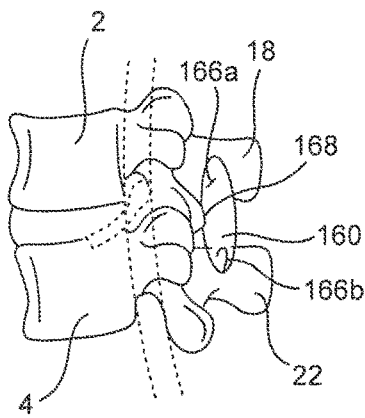
FIG. 16C

SYSTEMS AND METHODS FOR STABILIZING THE MOTION OR ADJUSTING THE POSITION OF THE SPINE

CROSS-REFERENCE TO RELATED APPLICATIONS

This application is a continuation of U.S. patent application Ser. No. 11/006,521, filed on Dec. 6, 2004, and entitled "SYSTEMS AND METHODS FOR STABILIZING THE MOTION OR ADJUSTING THE POSITION OF THE SPINE," which is a continuation in part of U.S. patent application Ser. No. 10/970,843, filed on Oct. 20, 2004, now U.S. Pat. No. 8,167,944, and entitled "SYSTEMS AND METHODS FOR POSTERIOR DYNAMIC STABILIZATION OF THE SPINE." Each of these applications is hereby incorporated by reference in its entirety.

FIELD OF THE INVENTION

The present invention is directed towards the treatment of spinal disorders and pain. More particularly, the present invention is directed to systems and methods of treating the spine to eliminate pain, adjust the position of one or more spinal motion segments and/or enable spinal motion which effectively mimics that of a normally functioning spine.

BACKGROUND OF THE INVENTION

FIG. 1 illustrates a portion of the human spine having a superior vertebra 2 and an inferior vertebra 4, with an intervertebral disc 6 located in between the two vertebral bodies. The superior vertebra 2 has superior facet joints 8a and 8b, inferior facet joints 10a and 10b, and spinous process 18. Pedicles 3a and 3b interconnect the respective superior facet joints a, 8b to the vertebral body 2. Extending laterally from superior facet joints 8a, 8b are transverse processes 7a and 7b, respectively. Extending between each inferior facet joints 10a and 10b and the spinous process 18 are laminal zones 5a and 5b, respectively. Similarly, inferior vertebra 4 has superior facet joints 12a and 12b, superior pedicles 9a and 9b, transverse processes 11a and 11b, inferior facet joints 14a and 14b, laminal zones 15a and 15b, and spinous process 22.

The superior vertebra with its inferior facets, the inferior vertebra with its superior facet joints, the intervertebral disc, and seven spinal ligaments (not shown) extending between the superior and inferior vertebrae together comprise a spinal motion segment or functional spine unit. Collectively, the facet joints, laminas and spinal processes comprise the "posterior element" (or a portion thereof) of a spinal motion segment. Each spinal motion segment enables motion along three orthogonal axes, both in rotation and in translation. The various spinal motions are illustrated in FIGS. 2A-2C. In particular, FIG. 2A illustrates flexion and extension motions and axial loading, FIG. 2B illustrates lateral bending motion and FIG. 2C illustrated axial rotational motion. A normally functioning spinal motion segment provides physiological limits and stiffness in each rotational and translational direction to create a stable and strong column structure to support physiological loads.

Traumatic, inflammatory, metabolic, synovial, neoplastic and degenerative disorders of the spine can produce debilitating pain that can affect a spinal motion segment's ability to properly function. The specific location or source of spinal pain is most often an affected intervertebral disc or facet joint. Often, a disorder in one location or spinal component can lead to eventual deterioration or disorder, and ultimately, pain in the other.

Spine fusion (arthrodesis) is a procedure in which two or more adjacent vertebral bodies are fused together. It is one of the most common approaches to alleviating various types of spinal pain, particularly pain associated with one or more affected intervertebral discs. While spine fusion generally helps to eliminate certain types of pain, it has been shown to decrease function by limiting the range of motion for patients in flexion, extension, rotation and lateral bending. Furthermore, the fusion creates increased stresses on adjacent non-fused motion segments and accelerated degeneration of the motion segments. Additionally, pseudarthrosis (resulting from an incomplete or ineffective fusion) may not provide the expected pain-relief for the patient. Also, the device(s) used for fusion, whether artificial or biological, may migrate out of the fusion site creating significant new problems for the patient.

Various technologies and approaches have been developed to treat spinal pain without fusion in order to maintain or recreate the natural biomechanics of the spine. To this end, significant efforts are being made in the use of implantable artificial intervertebral discs. Artificial discs are intended to restore articulation between vertebral bodies so as to recreate the full range of motion normally allowed by the elastic properties of the natural disc. Unfortunately, the currently available artificial discs do not adequately address all of the motion mechanics of the spinal column.

It has been found that the facet joints can also be a significant source of spinal disorders and debilitating pain. For example, a patient may suffer from arthritic facet joints, severe facet joint tropism, otherwise deformed facet joints, facet joint injuries, etc. These disorders lead to spinal stenosis, degenerative spondylolithesis, and/or isthmic spondylotlisthesis, pinching the nerves that extend between the affected vertebrae.

Current interventions for the treatment of facet joint disorders have not been found to provide completely successful results. Facetectomy (removal of the facet joints) may provide some pain relief; but as the facet joints help to support axial, torsional, and shear loads that act on the spinal column in addition to providing a sliding articulation and mechanism for load transmission, their removal inhibits natural spinal function. Laminectomy (removal of the lamina, including the spinal arch and the spinous process) may also provide pain relief associated with facet joint disorders; however, the spine is made less stable and subject to hypermobility. Problems with the facet joints can also complicate treatments associated with other portions of the spine. In fact, contraindications for disc replacement include arthritic facet joints, absent facet joints, severe facet joint tropism, or otherwise deformed facet joints due to the inability of the artificial disc (when used with compromised or missing facet joints) to properly restore the natural biomechanics of the spinal motion segment.

While various attempts have been made at facet joint replacement, they have been inadequate. This is due to the fact that prosthetic facet joints preserve existing bony structures and therefore do not address pathologies that affect facet joints themselves. Certain facet joint prostheses, such as those disclosed in U.S. Pat. No. 6,132,464, are intended to be supported on the lamina or the posterior arch. As the lamina is a very complex and highly variable anatomical structure, it is very difficult to design a prosthesis that provides reproducible positioning against the lamina to correctly locate the prosthetic facet joints. In addition, when facet joint replacement involves complete removal and replacement of the natural facet joint, as disclosed in U.S. Pat. No. 6,579,319, the prosthesis is unlikely to endure the loads and cycling experienced by the vertebra. Thus, the facet joint replacement may be subject to long-term displacement. Furthermore, when facet joint disorders are accompanied by disease or trauma to other structures of a vertebra (such as the lamina, spinous process, and/or transverse processes) facet joint replacement is insufficient to treat the problem(s).

Most recently, surgical-based technologies, referred to as "dynamic posterior stabilization," have been developed to address spinal pain resulting from more than one disorder, when more than one structure of the spine have been compromised. An objective of such technologies is to provide the support of fusion-based implants while maximizing the natural biomechanics of the spine. Dynamic posterior stabilization systems typically fall into one of two general categories: posterior pedicle screw-based systems and interspinous spacers.

Examples of pedicle screw-based systems are disclosed in U.S. Pat. Nos. 5,015,247, 5,484,437, 5,489,308, 5,609,636, 5,658,337, 5,741,253, 6,080,155, 6,096,038, 6,264,656 and 6,270,498. These types of systems involve the use of screws that are positioned in the vertebral body through the pedicle. Certain types of these pedicle screw-based systems may be used to augment compromised facet joints, while others require removal of the spinous process and/or the facet joints for implantation. One such system, the Zimmer Spine Dynesys® employs a cord which is extended between the pedicle screws and a fairly rigid spacer which is passed over the cord and positioned between the screws. While this system is able to provide load sharing and restoration of disc height, because it is so rigid, it does not effective in preserving the natural motion of the spinal segment into which it is implanted. Other pedicle screw-based systems employ articulating joints between the pedicle screws. Because these types of systems require the use of pedicle screws, implantation of the systems are often more invasive to implant than interspinous spacers.

Where the level of disability or pain to the affected spinal motion segments is not that severe or where the condition, such as an injury, is not chronic, the use of interspinous spacers are preferred over pedicle based systems as they require a less invasive implantation approach and less dissection of the surrounding tissue and ligaments. Examples of interspinous spacers are disclosed in U.S. Pat. No. Re. 36,211, U.S. Pat. Nos. 5,645,599, 6,149,642, 6,500,178, 6,695,842, 6,716,245 and 6,761,720. The spacers, which are made of either a hard or compliant material, are placed in between adjacent spinous processes. The harder material spacers are fixed in place by means of the opposing force caused by distracting the affected spinal segment and/or by use of keels or screws that anchor into the spinous process. While slightly less invasive than the procedures required for implanting a pedicle screw-based dynamic stabilization system, implantation of hard or solid interspinous spacers still requires dissection of muscle tissue and of the supraspinous and interspinous ligaments. Additionally, these tend to facilitate spinal motion that is less analogous to the natural spinal motion than do the more compliant and flexible interspinous spacers. Another advantage of the compliant/flexible interspinous spacers is the ability to deliver them somewhat less invasively than those that are not compliant or flexible; however, their compliancy makes them more susceptible to displacement or migration over time. To obviate this risk, many of these spacers employ straps or the like that are wrapped around the spinous processes of the vertebrae above and below the level where the spacer is implanted. Of course, this requires some additional tissue and ligament dissection superior and inferior to the implant site, i.e., at least within the adjacent interspinous spaces.

With the limitations of current spine stabilization technologies, there is clearly a need for an improved means and method for dynamic posterior stabilization of the spine and/or for treating scoliosis, which means and method address the drawbacks of prior devices. In particular, it would be highly beneficial to have a dynamic stabilization system that involves a minimally invasive implantation procedure, where the extent of distraction between the affected vertebrae is adjustable upon implantation and at a later time if necessary. It would be additionally advantageous if the system or device was also removable in a minimally invasive manner as well as obviated any risk of migration from the original implant site.

SUMMARY OF THE INVENTION

The present invention provides systems and methods for stabilizing or adjusting the position of at least one spinal motion segment. The systems are particularly useful in treating degenerative facet or disk disease, central and/or lateral canal stenosis, foraminal narrowing or any other condition which involves compression of the neural element. The systems are also useful in treating scoliosis.

The subject systems are implantable posterior to the spine in a minimally invasive manner and create or maintain distraction of at least a portion of the posterior element (i.e., the facet joints, laminas and/or the spinous processes) of the spinal motion segment being treated. The subject systems include one or more implantable members which are positionable laterally of the axial line or plane defined by the interspinous processes. In many embodiments, the lateral members are expandable in at least one dimension or direction, most commonly in a direction along the axis of the spine. The expandable members may be inflatable balloons, expandable scaffoldings or struts or the like or combination thereof. In certain embodiments, the expandable lateral members provide a distraction function between adjacent vertebrae or at least a portion of their posterior elements. In other embodiments, the expandable lateral members are used to maintain a distraction between the two vertebrae where the initial distraction is created by another means. This distraction involves relative movement between adjacent vertebrae where such movement may be axial (i.e., along the longitudinal axis of the spine) or angular or rotational (i.e., the angle defined by the intersection of the axes of two adjacent spinal processes is changed) or both.

Systems for addressing stabilization of a spinal segment, in certain embodiments, employ two lateral members in tandem where they are positioned on opposing sides of a single spinal motion segment. These types of systems are referred to herein interchangeably as "bi-lateral" or "para-lateral" systems. Certain of these systems further employ one or more intermediately positioned transverse members extending between the two, laterally-opposed members. The transverse member(s) may varying in number and function and may couple with the lateral members in any suitable manner and at any point along a dimension, e.g., the length, of the lateral members.

In certain embodiments, two transverse members may be placed at opposing end portions of the lateral members and may also be configured to engage the spinous processes in some manner. In one variation, the transverse members may be configured to engage an outer surface of a spinous process, and as such, act as a saddle or cradle. In another variation, the transverse member is configured to engage a surface formed within the spinous process, i.e., is positioned within and extended through a width of a spinous process where a through bore or hole is made from one side of the process to the other.

In other embodiments, only a single transverse member is employed. In one variation of this embodiment, the transverse member extends substantially centrally between the two lateral members and the size, e.g., height, of the single transverse member dictates whether or not the transverse member engages one or both of the spinous processes between which it is interposed. For example, the transverse member may have a planar or webbing configuration with its end portions configured to engage the spinous processes and act as a saddle or cradle. On the other hand, the transverse member may be fairly narrow in width wherein it does not engage the spinous processes between which it extends and is configured as a lumen or the like which interconnects the two lateral members in fluid communication with each other. Thus, the material used to fabricate the transverse members, their size and extent of flexibility and the position in which they are placed relative to the lateral members and the other transverse members are primarily dictated by the intended function of the transverse members.

The lateral members and transverse members may be positioned substantially perpendicular to one another or their interconnection may define an acute or obtuse angle between the two. Where there are two or more transverse members, they may be positioned parallel to each other or they themselves may intersect at an angle.

In certain other embodiments of the present invention, only a single expandable member is used or is necessary to treat a single spinal segment where the member is positioned on either the left or right side of the spinal motion segment being treated. These types of systems are referred to herein as "unilateral" systems. Such systems are particularly useful in treating spinal motion segments where one side is more symptomatic than the other, for example, where bony spur deposits create a hypertrophic facet joint or due to foraminal narrowing. The systems are also useful for treating scoliosis.

A plurality of such unilateral members may be placed along and on either or both sides of the spine as necessary. For example, where the spinal condition affects several adjacent spinal segments, a plurality of lateral members aligned in a serial fashion along the same or both sides of the spine may be employed. For spinal motion stabilization applications, two unilateral systems may be employed in tandem with respect to the same spinal segment where they are positioned on opposite sides of the spine. Such an arrangement may be used to stabilize spinal motion similar to the bi-lateral approach described above with the difference being that the two "unilateral" members are not interconnected or integral with each other in any way.

The function of a lateral member of a unilateral system may depend on its particular placement relative to the components of the posterior element of the spinal motion segment being treated. For example, the lateral member may be positioned relatively anteriorly, e.g., between the laminal portions, and configured to engage with the same. As such, the lateral member provides a distracting function which may then require use of an anchoring means within the implant site to secure the lateral member to a portion of the vertebrae so as to minimize the risk of migration of the lateral member. Such anchoring means may include one or more transverse members which interconnect with one or both of the spinal processes. Alternatively, one or more transverse members may be configured and aligned to interconnect with one or more portions of the lamina or one or more facet joints of the spinal segment being treated. Still, yet one transverse member may anchor to a spinous process and the other may anchor to a lamina or facet joint. On the other hand, the lateral member may be positioned relatively posteriorly within the muscle and fascial tissue and itself be an anchoring means for another component which functions as a distracting means.

Distraction between the adjacent vertebrae of the spinal segment being treated by a bi-lateral system or by two unilateral systems implanted at the same spinal motion segment is primarily in the axial direction of the spine. It should be understood that the axial distraction may be accomplished by the lateral members themselves but such is not always or necessarily the case. Instead, while the lateral members may contribute to maintaining a distracting force between the adjacent vertebrae, the initial distraction may be created by a separate distraction means which itself may also have an expandable component. The transverse member(s) of the implantable system is (are) then employed, in some cases, to maintain the distraction, while the lateral members essentially anchor the transverse member(s). While distraction between adjacent vertebrae of a spinal segment being treated by a unilateral system of the present invention is primarily rotational or angular, the same distracting-anchoring relationship may exist between the lateral member and the one or more transverse members in a unilateral approach.

The expandable lateral members of the present invention have an unexpanded configuration and an expanded configuration, wherein the expandable member in an expanded configuration has a size, volume and/or shape configured for positioning minimally invasively in a position lateral to a spinous process. The expandable member may include an enclosed cavity which is fillable with a material to effect expansion or may have a strut or scaffolding-like structure that has a low profile configuration for delivery purposes through a small working channel and which is expandable to a greater profile upon deployment at or in close proximity to the implant site.

The former type of expandable members include inflatable balloons made of either non-compliant or compliant material, may include a mesh material which may be coated or lined with a non-porous material or may generally provide an enclosed, compressible cavity which is fillable with a material such as a gas, fluid or other material which is deliverable in a flowable form which subsequently forms a solid upon curing, setting or drying. The expandable member may further include a port for coupling to a source of inflation and/or an expansion medium for inflating and/or expanding the expandable member. In certain embodiments, the port may be used to deflate or evacuate the expandable member.

The latter type of expandable members may have a preformed configuration which is compressible and which is self-expanding upon deployment. Alternatively, the expandable members may be selectively adjustable and locked into place upon achieving a certain degree of expansion.

Optionally, the systems may include one or more markers on a surface of a lateral and/or transverse member to facilitate fluoroscopic imaging during minimally invasive implantation, particularly percutaneous implantation.

The invention further includes methods directed to stabilizing or adjusting the position of at least one spinal motion segment. The methods involve the implantation of one or more systems of the present invention, in which a lateral member is positioned laterally of a spinal motion segment in an unexpanded condition and then subsequently expanded to a size and/or shape for maintaining a selected distraction of adjacent vertebrae of a spinal motion segment. The invention also contemplates the temporary implantation of the subject systems which may be subsequently removed from the patient once the intended treatment is complete. Many of the methods involve the percutaneous implantation of the subject systems.

These and other objects, advantages, and features of the invention will become apparent to those persons skilled in the art upon reading the details of the invention as more fully described below.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures:

FIGS. 2A, 28 and 2C illustrate left side, dorsal and top views, respectively, of the spinal segments of FIG. 1A under going various motions.

FIGS. 11A-11H illustrate the steps of implanting the bi-lateral posterior element distraction system of FIGS. 10A-10C.

FIGS. 12A-12E illustrate the steps of implanting another bi-lateral posterior element distraction system of the present invention.

FIGS. 16A and 16B illustrate dorsal views of another bi-lateral posterior element distraction system of the present invention implanted within a spinal motion segment in unexpanded and expanded configurations, respectively. FIG. 16C is a side view of the posterior element distraction system of FIG. 16B.

DETAILED DESCRIPTION OF THE INVENTION

Figure 1:
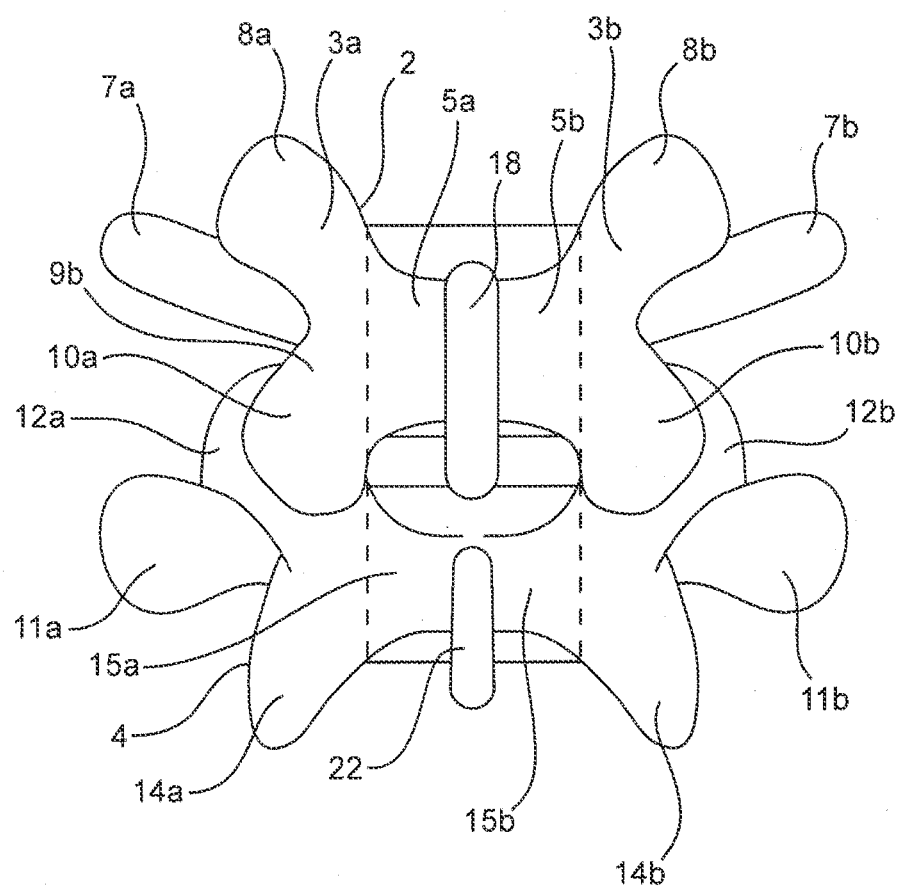
FIG. 1 illustrates a perspective view of a portion of the human spine having two vertebral segments.
Figure 2A:
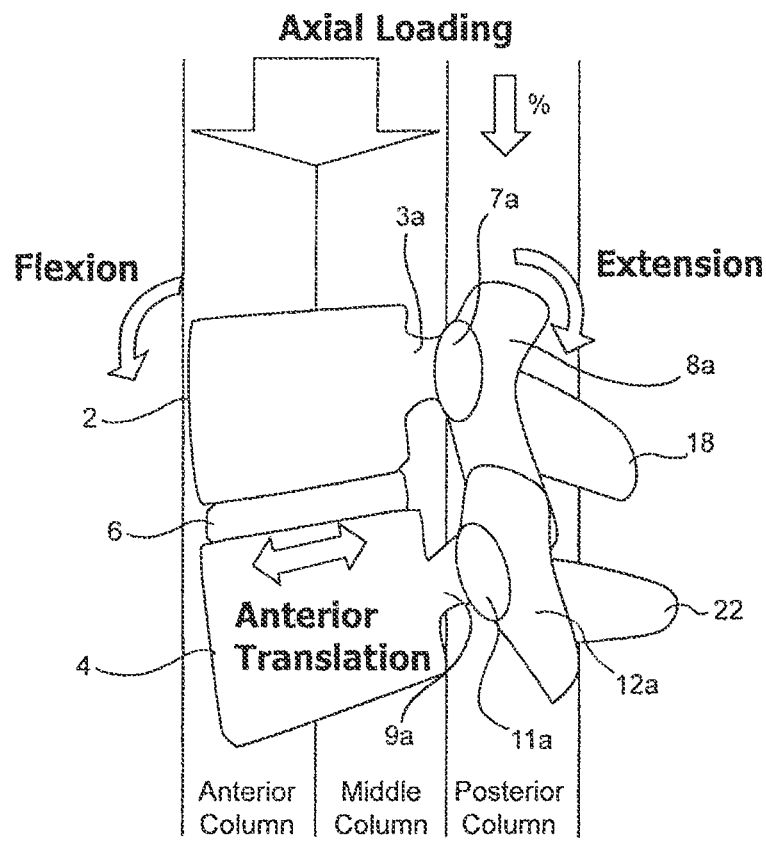
Figure 2B:
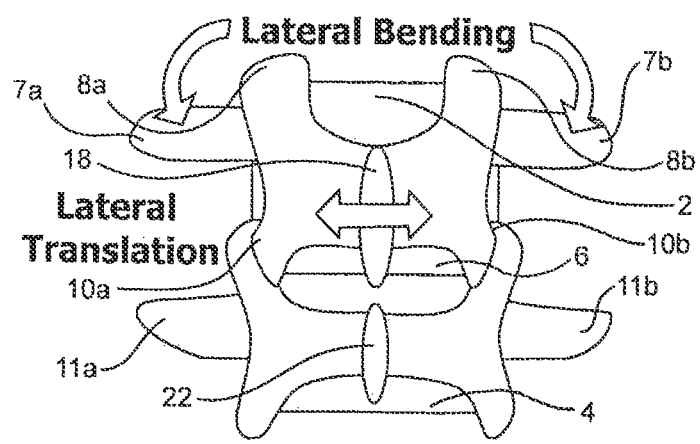
Figure 2C:
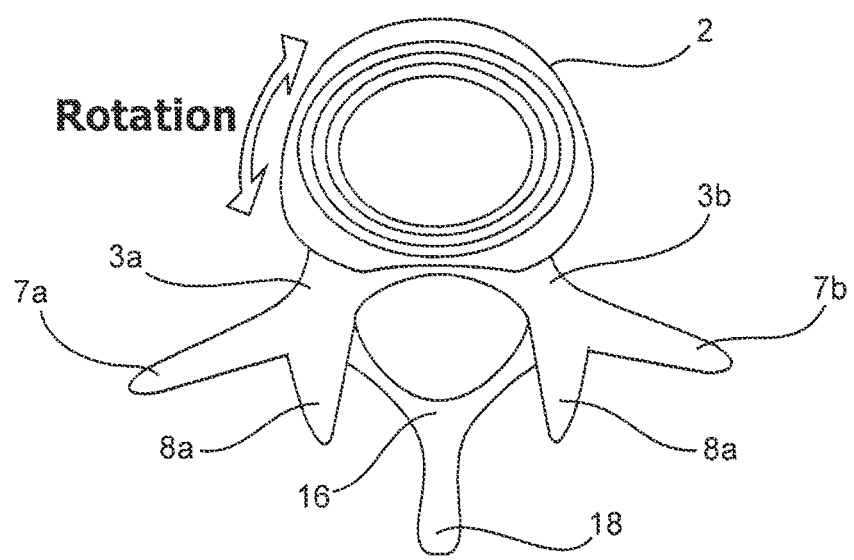

Before the subject devices, systems and methods are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs.

It must be noted that as used herein and in the appended claims, the singular forms "a", "an", and "the" include plural referents unless the context clearly dictates otherwise. Thus, for example, reference to "a spinal segment" may include a plurality of such spinal segments and reference to "the screw" includes reference to one or more screw and equivalents thereof known to those skilled in the art, and so forth.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The present invention will now be described in greater detail by way of the following description of exemplary embodiments and variations of the devices and methods of the present invention. The invention generally includes an implantable system or device as well as instruments for the percutaneous implantation of the system or device. A key feature of the subject systems is that it includes an expandable member which is implanted laterally of a spinal motion segment. In many embodiments the lateral member is expandable from a low profile configuration to a higher profile or operative configuration. This design allows the lateral member, when in the low profile condition, to be delivered by percutaneous means without requiring the removal of any portion of the spinal motion segment into which the device is implanted.

Figure 3A:
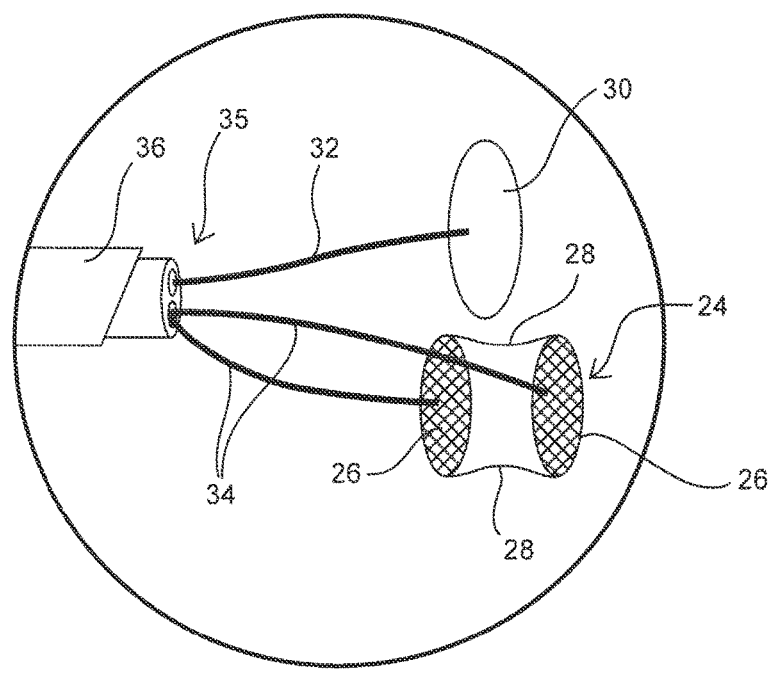
FIG. 3A illustrates a bi-lateral posterior element distraction system of the present invention operatively engaged within a delivery and implantation system of the present invention.

Referring now to the drawings and to FIG. 3A in particular, an exemplary bilateral posterior element distraction system 24 of the present invention. System 24 includes parallely spaced apart expandable lateral members 26 and transverse members 28 extending between the end portions of lateral members 26. Here, lateral members 26 are illustrated as balloons (shown in an expanded condition) encased in an optional mesh material. The balloons may be made of a non-porous, biocompatible material, such as latex or acrylate. The balloons are inflatable with an inflation or expansion medium, such as air, saline, another biologically compatible fluid, or a flowable solid material, such as polyurethane, or a gel, which thickens or hardens substantially upon injection into balloon the balloon. Alternatively, the balloons may be made of a porous material, such as a hydrophilic polymer, to allow absorption of fluid from the implant site to within the balloon. The extent of expansion of the balloons is dependent upon the particular composition of the hydrophilic polymer used.

In certain embodiments, the balloons are made of a non-compliant or semi-compliant material so as to maintain a substantially fixed shape or configuration and ensure proper, long-term retention within the implant site. In other embodiments, the balloons may be made of a compliant material. In any embodiment, the compressibility and flexibility of balloons 26 can be selected to address the indications being treated. Optionally still, balloons 26 may further include radiopaque markers (not shown) on their surfaces which are visible under fluoroscopic imaging to facilitate positioning of system 24. The optional mesh material may be made of a material similar to that of the balloons, polyethylene, a metal, e.g., a nitinol or titanium, or another compliant (stretchable) or non-compliant material to provide a protective layer about the balloons to provide further stability to the balloons. For purposes of fluoroscopic imaging, the mesh material itself may be radiopaeque.

Transverse members 28 may be made of a metal or polymer material that is conformable to a solid structure, e.g., a spinous process 18, 22 (see FIG. 3C), against which it is placed in tension and has a sufficient length and width to contact at least a portion of the spinous process. The distance between the two transverse members 28 and the length of each may vary depending on the extent of distraction desired between the vertebrae of the spinal motion segment into which the system is implanted.

FIG. 3A illustrates posterior element distraction system 24 operatively engaged to a minimally invasive delivery and implantation system 35 of the present invention. System 35 includes a main body 36 which defines a working channel within proximity of the implant site and further includes a lumen for the delivery of system 24 when in an unexpanded configuration to within proximity of the implant site. In this embodiment, each of balloons 26 is fluidly coupled to an inflation line 34 which also functions as a pusher for advancing the balloons collectively through the main body lumen and for advancing it once in the implant region. System 35 further includes a distraction mechanism 30, also in the form of an expandable balloon. Distraction balloon is also fluidly coupled to an inflation line 32 which, like lines 34, also functions as a pusher for advancing balloon 30 through the main body lumen. Distraction mechanism 30 may share a single lumen with system 24 or may be deliverable through its own designated lumen. Air and saline are suitable mediums for inflating the distraction balloon.

Figure 3B:
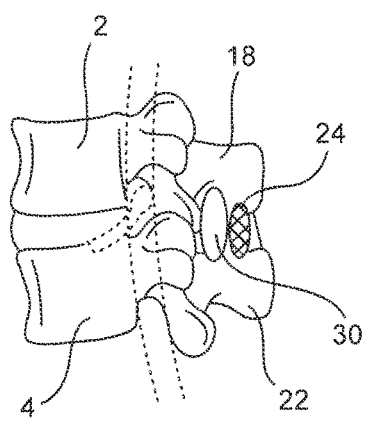
FIG. 3B is a side view of the posterior element distraction system and a distracting mechanism of the implantation system of FIG. 3A positioned within a spinal motion segment.

In use, and subsequent to the preparatory steps taken as will be described below with respect to FIGS. 26A-26E, delivery body 36 is inserted to within proximity to the implant site of the spinal motion segment being treated. Upon insertion, distraction mechanism 30 is translated in an unexpanded or deflated state through main body 36. In addition to advancing distraction balloon 30, inflation lumen 32 acts as a guide wire to direct distraction balloon to within the interspinous space of the spinal segment being treated. In particular, distraction balloon 30 is placed substantially anteriorly within the space. Upon proper positioning within the interspinous space, distraction balloon 30 is slowly inflated to progressively distract the spinous processes 18, 22, as illustrated in FIG. 3B. Upon sufficient distraction of the vertebrae 2, 4, system 24 is similarly advanced to within the interspinous space adjacent and posteriorly to the distraction balloon 30; however, the relative position of the implanted balloons and the temporary distraction balloons may be reversed, depending on the particular application at hand. Upon proper alignment within the space, balloons 26 are inflated or expanded and transverse members 28 are caused to engage respective spinous processes 18 and 22. Balloons 26 are inflated to the extent necessary to maintain the desired distraction of vertebrae 2, 4. Distraction balloon 30 is then deflated and retracted from the interspinous space, and inflation lumens 34 are decoupled from balloons 26 and retracted to within main body 36.

Figure 3C:
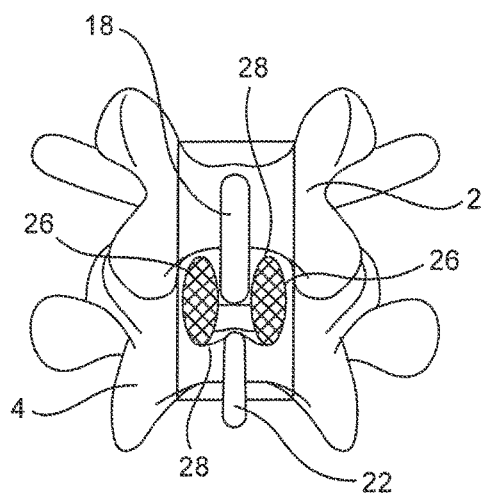
FIG. 3C is a dorsal view of the posterior element distraction system of FIG. 3A implanted within the spinal motion segment.

FIG. 3C illustrates system 24 operatively implanted within a spinal motion segment having superior vertebra 2 and inferior vertebra 4 where lateral members 26 are positioned on opposite sides of the interspinous space and transverse members 28 extend across the interspinous space and are in contact with opposing spinous processes 18, 22, respectively. As such, transverse members 28 maintain the posterior element distraction achieved by distraction mechanism 30 and lateral members 26 function to anchor the transverse members 28.

Figure 4A:
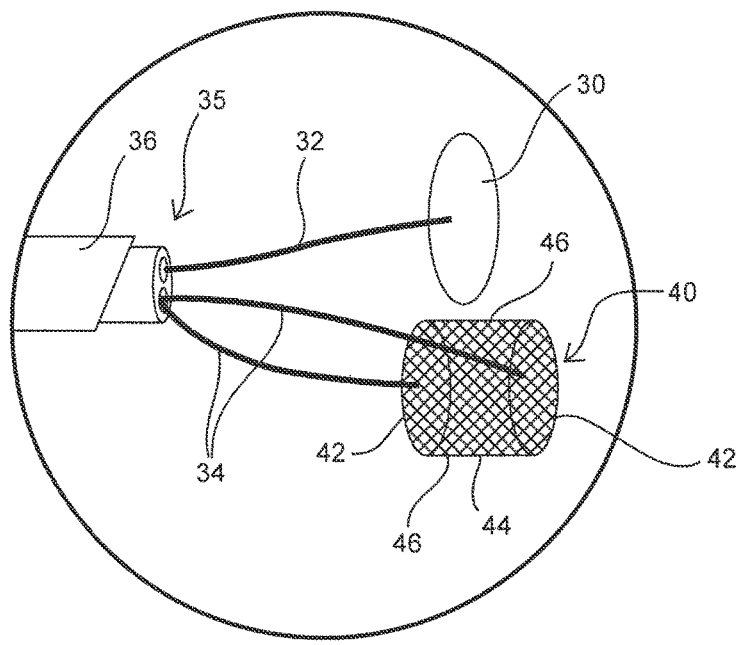
FIG. 4A illustrates another bi-lateral posterior element distraction system of the present invention operatively engaged within a delivery and implantation system of the present invention.
Figure 4B:
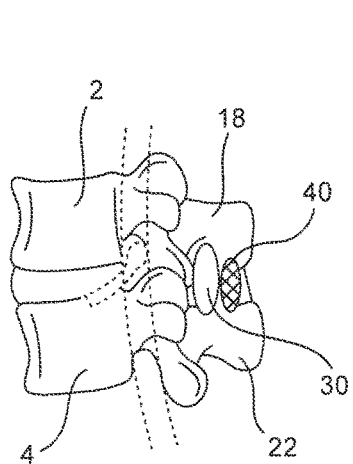
FIG. 4B is a side view of the posterior element distraction system and a distracting mechanism of the implantation system of FIG. 4A positioned within a spinal motion segment.
Figure 4C:
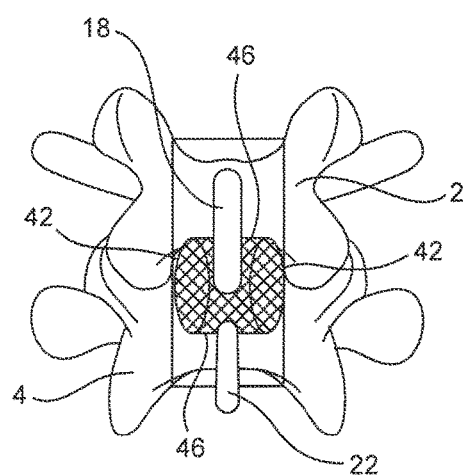
FIG. 4C is a dorsal view of the posterior element distraction system of FIG. 4A implanted within the spinal motion segment.

Another embodiment of an implantable posterior element distraction system of the present invention is illustrated in FIGS. 4A-4C. System 40 also includes expandable lateral members 42 in the form of balloons. A single fitted mesh 44 is provided over and encases both balloons in opposing manner with the peripheral edges 46 of mesh 44 functioning as transverse members. System 40 is implantable and deployable in the same manner as described above with respect to system 24 of FIGS. 3A-3C.

Figure 5A:
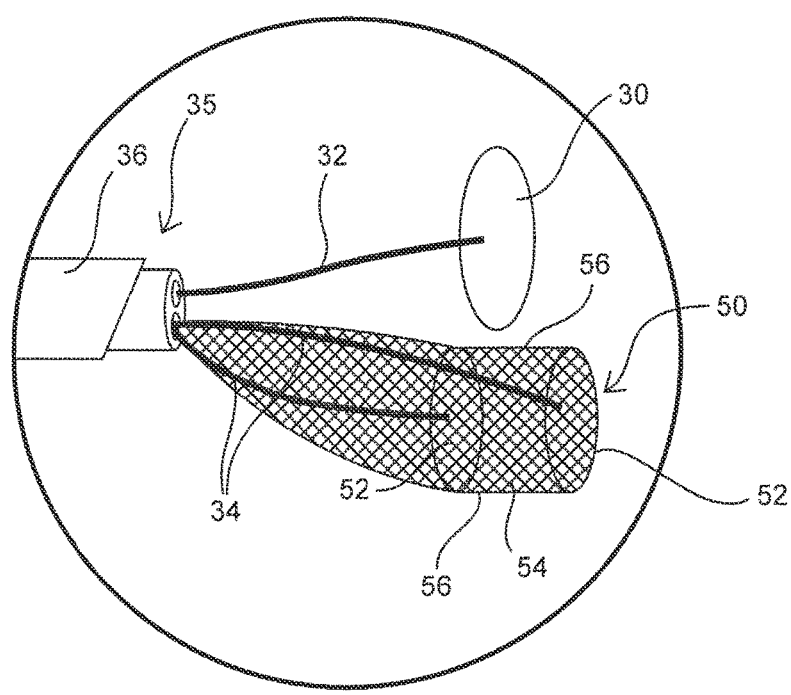
FIG. 5A illustrates another bi-lateral posterior element distraction system of the present invention operatively engaged within a delivery and implantation system of the present invention.
Figure 5B:
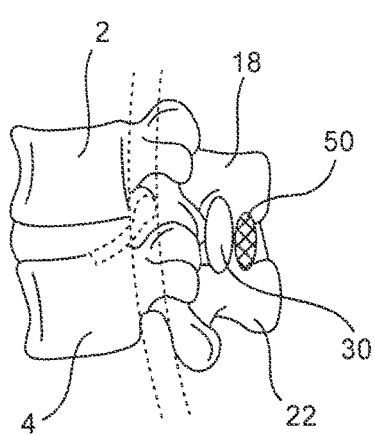
FIG. 5B is a side view of the posterior element distraction system and a distracting mechanism of the implantation system of FIG. 5A positioned within a spinal motion segment.
Figure 5C:
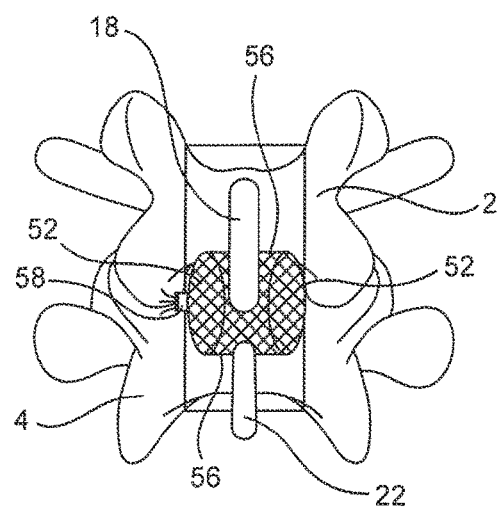
FIG. 5C is a dorsal view of the posterior element distraction system of FIG. 5A implanted within the spinal motion segment.

Another embodiment of an implantable posterior element distraction system of the present invention is illustrated in FIGS. 5A-5C. System 50 provides expandable lateral members 52 similar to those just described and enclosed in a mesh 54. Here, however, instead of a fitted mesh, mesh 54 is in the form of a sock which is open at a proximal end and extends over inflation lumens 34. Subsequent to delivery, deployment and inflation of lateral members 52 within the implant site between the interspinous processes, 18, 22 (as described above with respect to FIGS. 3A-3C), the open proximal end of mesh 54 is synched down to tightly encase balloons 52. Upon proper tensioning between the balloons, the synched end 58 is tied or secured and the proximally extending remainder is cut and removed. To accomplish such, implantation system 35 is equipped with synching and cutting mechanisms (not shown) which may be deliverable to the target site through designated lumens within main body 36. As with the posterior element distraction system of FIG. 4A-4C, the now taught peripheral edges 56 of mesh 54 function as transverse members.

Figure 6A:
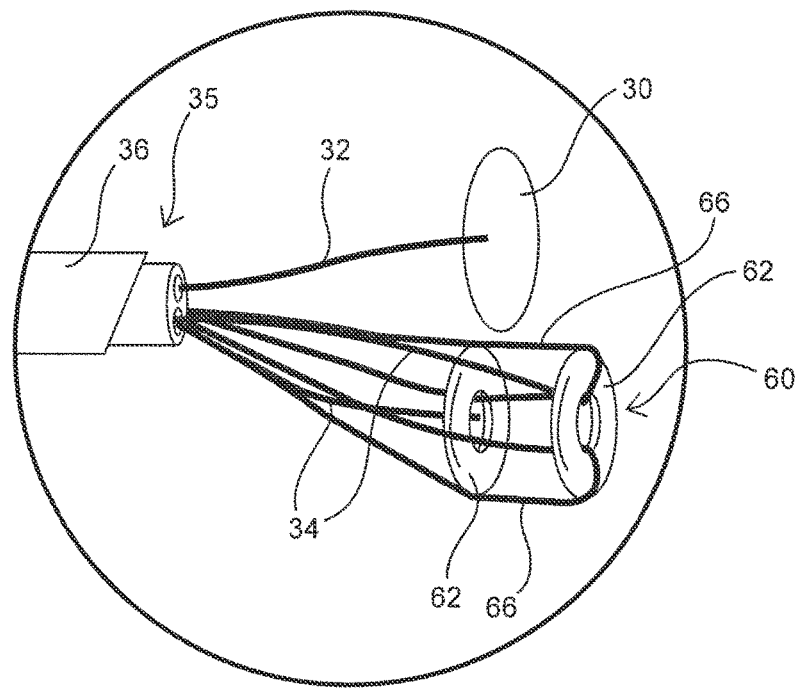
FIG. 6A illustrates another bi-lateral posterior element distraction system of the present invention operatively engaged within a delivery and implantation system of the present invention.
Figure 6B:
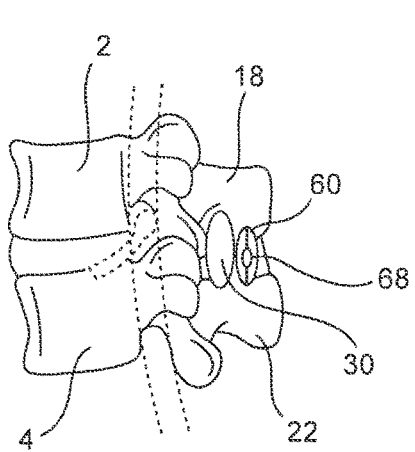
FIG. 6B is a side view of the posterior element distraction system and a distracting mechanism of the implantation system of FIG. 6A positioned within a spinal motion segment.
Figure 6C:
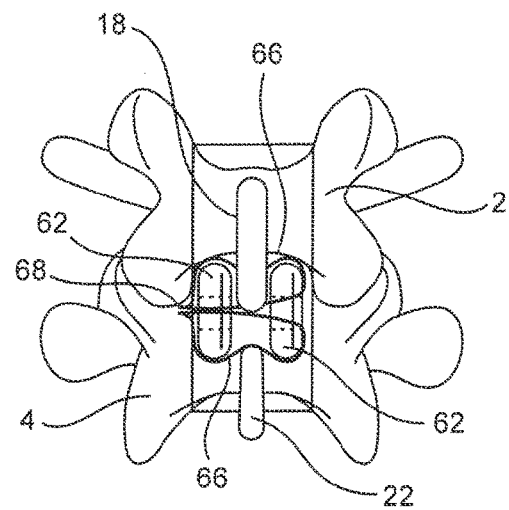
FIG. 6C is a dorsal view of the posterior element distraction system of FIG. 6A implanted within the spinal motion segment.

FIGS. 6A-6C illustrate another posterior element distraction system 60 in which lateral members 62 are in the form of doughnut-shaped balloons. Balloons 62 are maintained in an opposed substantially parallel relationship with each other by way of straps 66 wherein each strap 66 is wrapped around opposing sides of balloons 62. The two ends of each strap 66 and balloon inflation lines 34 then collectively extend proximally together to within the same delivery lumen of main body 36 of implantation system 35. System 60 is implanted as described with respect to FIGS. 3A-3C, and upon proper implantation of balloons 62, the strap ends 68 are synched and cut as described above. As illustrated in FIG. 6C, the outer portion of straps 66 function as transverse members, maintaining the distraction achieved by distraction mechanism 30.

Figure 7A:
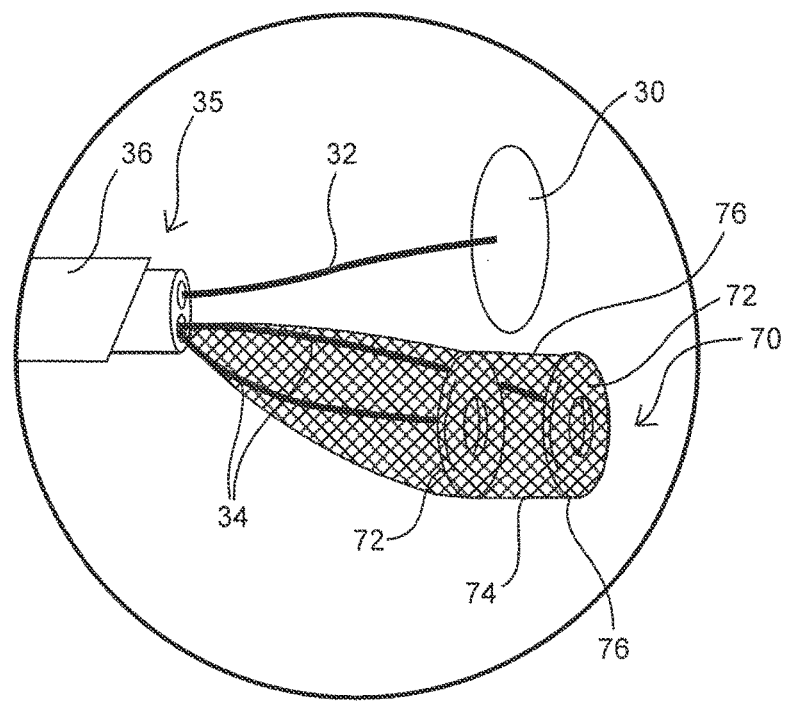
FIG. 7A illustrates another bi-lateral posterior element distraction system of the present invention operatively engaged within a delivery and implantation system of the present invention.
Figure 7B:
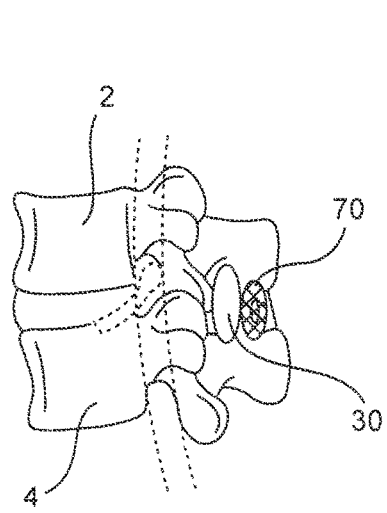
FIG. 7B is a side view of the posterior element distraction system and a distracting mechanism of the implantation system of FIG. 7A positioned within a spinal motion segment.
Figure 7C:
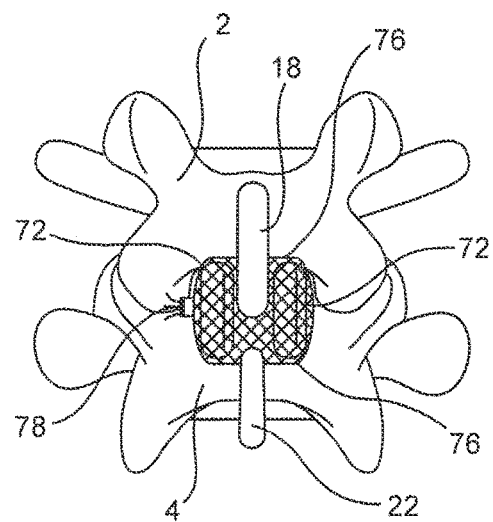
FIG. 7C is a dorsal view of the posterior element distraction system of FIG. 7A implanted within the spinal motion segment.

The posterior element distraction system 70 of FIGS. 7A-7C involves features of the systems of FIGS. 5A-5C and FIGS. 6A-6C in that the lateral members 72 of system 70 are doughnut-shaped balloons enclosed in a mesh sock 74. Similar to the system of FIGS. 5A-5C, upon proper implantation within the implant site, the proximal end 78 of mesh 74 is synched and cut to maintain balloons 72 in a tensioned, substantially parallel relationship with peripheral edges 76 of mesh 74 functioning as transverse members.

Figure 8A:
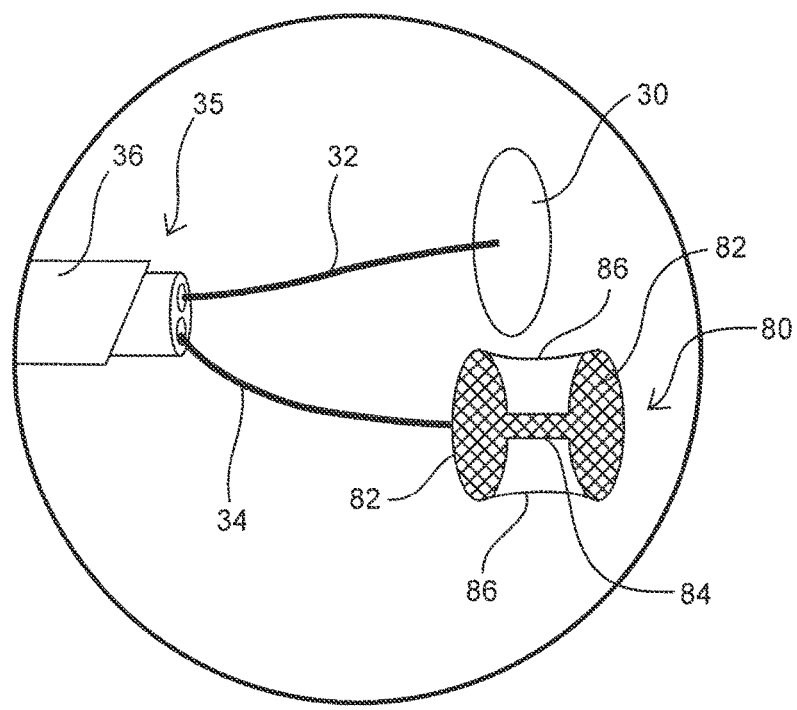
FIG. 8A illustrates another bi-lateral posterior element distraction system of the present invention operatively engaged within a delivery and implantation system of the present invention.
Figure 8B:
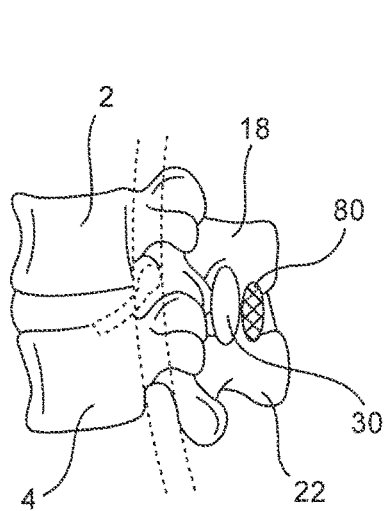
FIG. 8B is a side view of the posterior element distraction system and a distracting mechanism of the implantation system of FIG. 8A positioned within a spinal motion segment.
Figure 8C:
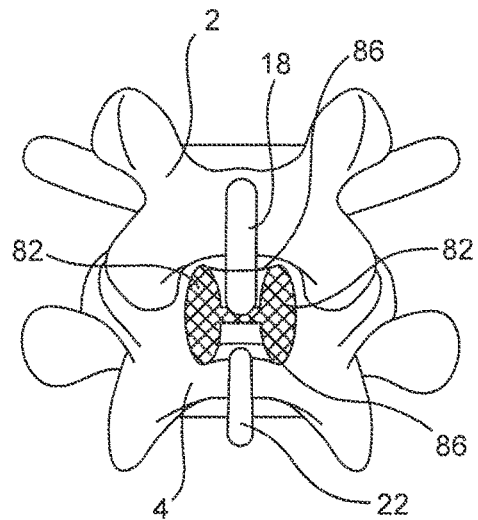
FIG. 8C is a dorsal view of the posterior element distraction system of FIG. 8A implanted within the spinal motion segment.

FIGS. 8A-8C illustrate another embodiment of a posterior element distraction system 80 having inflatable lateral members 82 fluidly interconnected at a central location by transverse member 84. Transverse member 84 is in the form of a lumen thereby eliminating the need for separate inflation lumens 34 for balloons 82. Only a single inflation lumen 34, here coupled to the more proximal of the two balloons 82, as lumen 84 transports the inflation medium from the proximally positioned balloon to the distally positioned balloon. System 80 further includes transverse member 86 which are configured to engage and maintain the distraction between the spinous processes 18, 22. System 80 is implanted as described with respect to FIGS. 3A-3C.

Figure 9A:
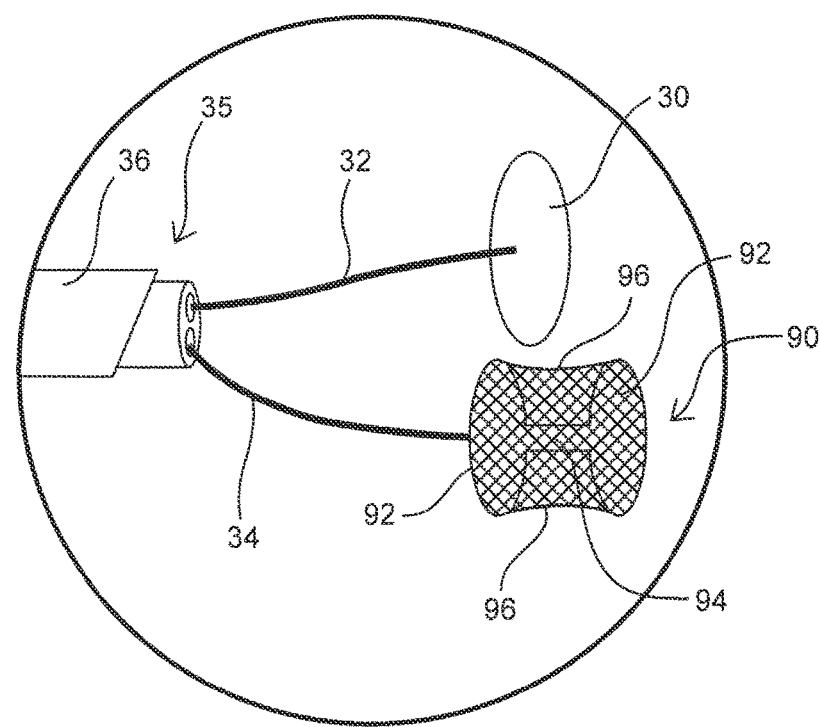
FIG. 9A illustrates another bi-lateral posterior element distraction system of the present invention operatively engaged within a delivery and implantation system of the present invention.
Figure 9B:
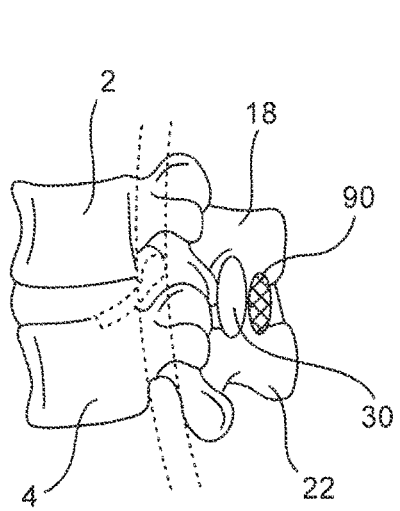
FIG. 9B is a side view of the posterior element distraction system and a distracting mechanism of the implantation system of FIG. 9A positioned within a spinal motion segment.
Figure 9C:
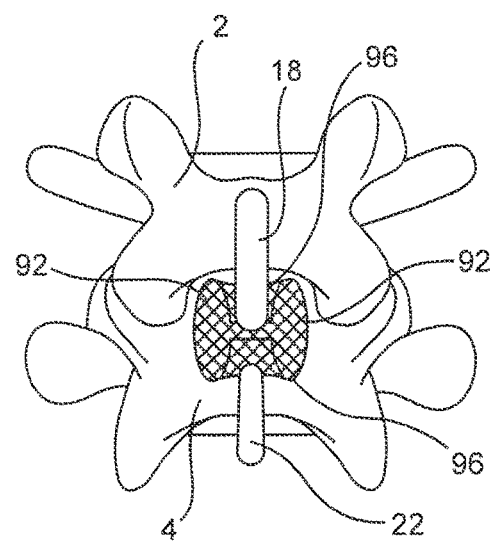
FIG. 9C is a dorsal view of the posterior element distraction system of FIG. 9A implanted within the spinal motion segment.

FIGS. 9A-9C illustrate another embodiment of a posterior element distraction system 90 having inflatable lateral members 92 fluidly interconnected at a central location by transverse member 94. Similar to that of the system of FIGS. 8A-8C, transverse member 94 is in the form of a lumen for transporting the inflation medium from the proximally positioned balloon to the distally positioned balloon. A single fitted mesh 94 is provided over and encases both balloons 92 in an opposing manner with the peripheral edges 96 of mesh 94 functioning as transverse members. System 90 is implantable and deployable in the same manner as described above with respect to FIGS. 3A-3C.

Figure 10A:
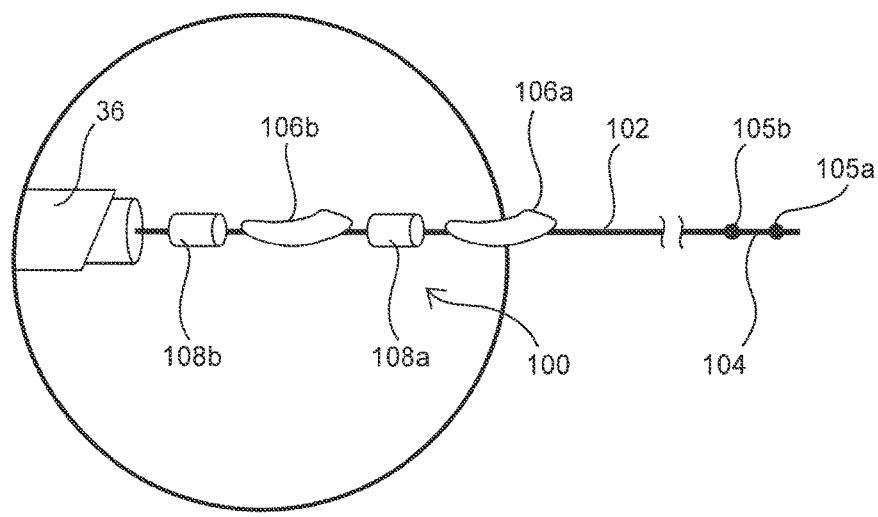
FIG. 10A illustrates another bi-lateral posterior element distraction system of the present invention operatively engaged within a delivery and implantation system of the present invention.
Figure 10B:
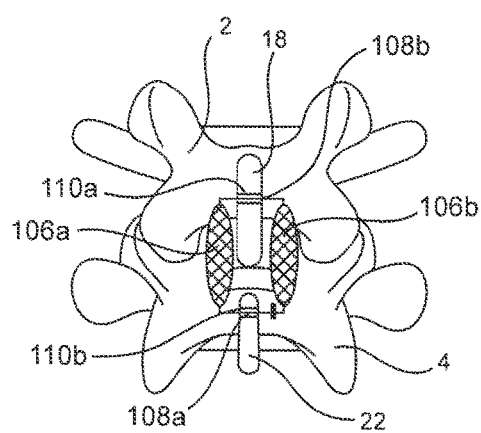
FIG. 10B is a dorsal view of the posterior element distraction system of FIG. 10A implanted within a spinal motion segment.
Figure 10C:
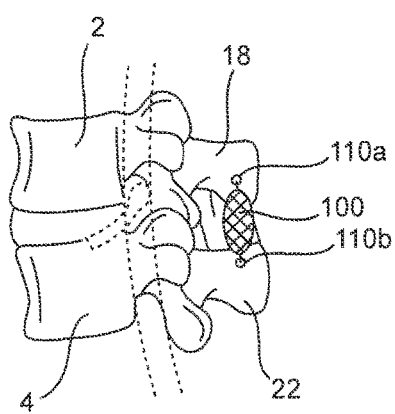
FIG. 10C is a side view of FIG. 10A.

FIGS. 10A-10C illustrate another posterior element distraction system 100 of the present invention. System 100 includes lateral members 106a, 106b and transverse members 108a, 108b provided serially on a guide wire 102 where each component is fixedly coupled to guide wire or suture thread 102. Guide wire 102 has a leading distal end 104 configured to facilitate threading or feeding of system 100 through the bone and tissue at the implant site. For example, distal end 104 may have a dumbbell configuration with bulbous end portions 105a, 105b particularly suited for being held by a feeding or threading tool 117 which is described below with respect to FIGS. 11B and 11C. Lateral members 106a, 106b are inflatable balloons which may have any material composition and configuration as described above. Transverse members 108a, 108b are in the form of cylindrical plugs and may be made of a metal, polymer or the like and may be coated with hydroxyapetate to facilitate bone in growth. The coating may also include a lubricant to facilitate delivery through the spinous process as will be explained in greater detail below.

Figure 11F:
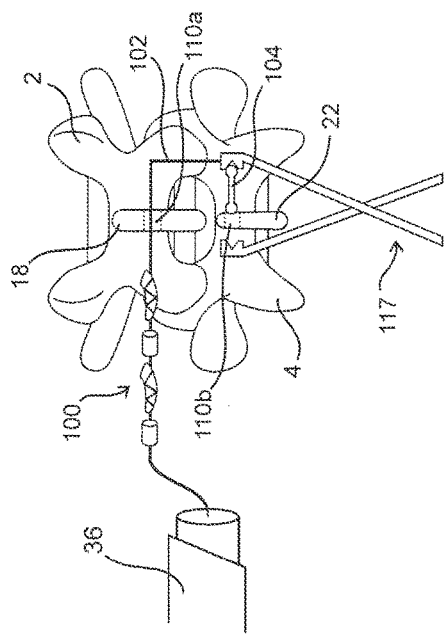
Figure 11E:
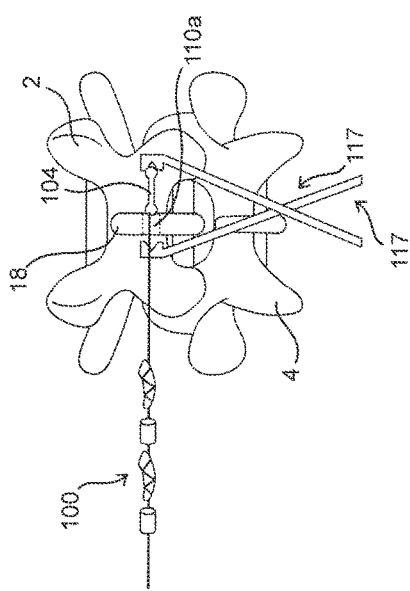
Figure 11H:
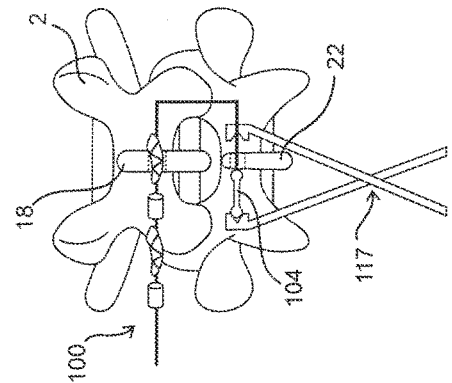
Figure 11G:
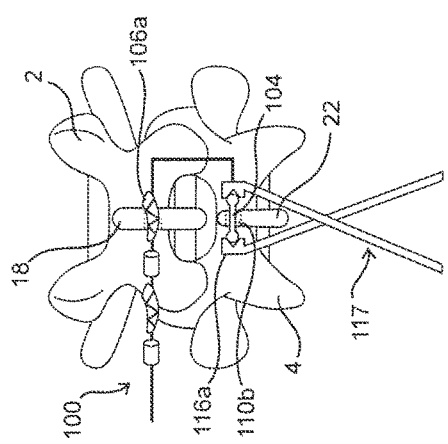

FIGS. 11A-11H illustrate the various steps involved in implanting distraction system 100 at a target site within a spinal motion segment. Generally, system 100 is implanted by threading guide wire 102 through hole or bores which are formed in both spinous processes 18, 22 of the spinal motion segment. To begin, a small incision is made proximate the target spinal motion segment in order to access spinous processes 18, 20. As illustrated in FIGS. 11A and 11B, a puncturing or hole-forming tool 115 is used to form bores 110a, 110b within spinous process 18, 22, respectively. Tool 115 has opposing jaws 112a, 112b where jaw 112a has punch member and jaw 112b has an anvil configuration for receiving the punch member. Distal end 104 is then operatively loaded into guide wire feeding tool 117 as shown in FIG. 11C and the jaws of feeding tool 117 are straddled on the opposite sides of spinous process 18. Specifically, distal bulb 105a of feeding end 104 is held in the left jaw 116a of feeding tool 117 and distal bulb 105b is fed through bore 110a in superior spinous process 18 and is received in right jaw 116 which is positioned on the opposing side of spinous process 18, as shown in FIG. 11D. During this step, guide wire 102 is folded back over leading end 104 and, as such, is threaded through bore 10a as well. Guide wire 102 is pulled through bore 110a (FIG. 11E) and then tool 117 is repositioned closer to inferior spinous process 22 where distal bulb 105a of leading end 104 is inserted in to bore 110b (FIG. 11F) and received on the opposing side by jaw 116a of tool 117 (FIG. 11G). Guide wire 102 is then pulled through both bores 110a, 110b (FIG. 1H) until system 100 is positioned as illustrated in FIGS. 10B and 10C. Namely, distal balloon 106a in on the left side of the interspinous space, proximal balloon 106b is on the right side of the interspinous space, distal bore plug 108a is positioned within bore 110a of spinous process 22 and bore plug 108b is positioned within bore 110b of spinous process 18. The distal portion of guide wire 102 situated between distal balloon 106b and leading end 104 and the proximal portion of guide wire 102 proximal to balloon 108b are cut. The cut ends are then securely fixed together such as by tension crimpers. Either before or after the guide wire is cut, balloons 106 are inflated or expanded by a separate inflation means (not shown). Alternatively, guide wire 102 may be equipped with a central inflation lumen, in which case, inflation of the balloons must occur before cutting the guide wire.

FIGS. 12A-12E illustrate another bi-lateral posterior element distraction system 130 and the steps for implanting it within a target spinal motion segment. Like the system of FIGS. 11A-11C, the components of system 120 are serially interconnected to a guide wire 128 which is deliverable through implantation system 36. System 120 includes lateral balloon members 122 and transverse members 124 which are interconnected with each other via a preformed, compressible annular strut 124 which itself is interconnected to guide wire 128. On opposing sides of system 120, in particular on the outer sides of balloons 122 are balloon abutment members 129 such that each balloon 122 is sandwiched between a side of strut 124 and an abutment member. System 120 is deliverable from one side of the target spinal motion segment, and is inserted through the interspinous space while strut 124 is in a restrained or compressed state until transverse members 126 are centered between the spinous processes 18, 22, as shown in FIG. 12B. Then, strut 124 is allowed to expand to is preformed, expanded state, as shown in FIG. 12C. Subsequently, balloons 122 are inflated so as to expand both vertically and widthwise and are caused to contact and become snuggly fit between their respective abutment member 129 and strut 124, as illustrated in FIG. 12D. Balloons 122 preferably have a cogged, petalled or starred configuration to better anchor within the surrounding tissue and, thus, mitigate migration of the device.

Figure 13A:
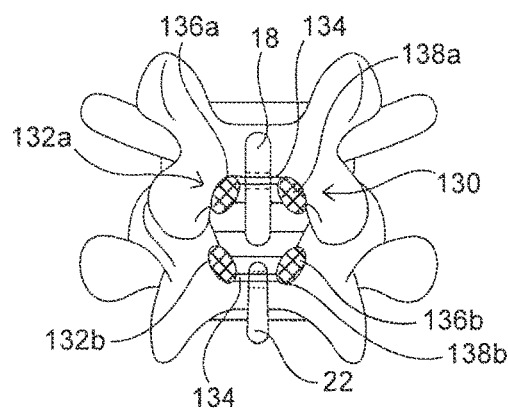
FIGS. 13A and 13B illustrate dorsal views of another bi-lateral posterior element distraction system of the present invention implanted within a spinal motion segment in unexpanded and expanded configurations, respectively.
Figure 13B:
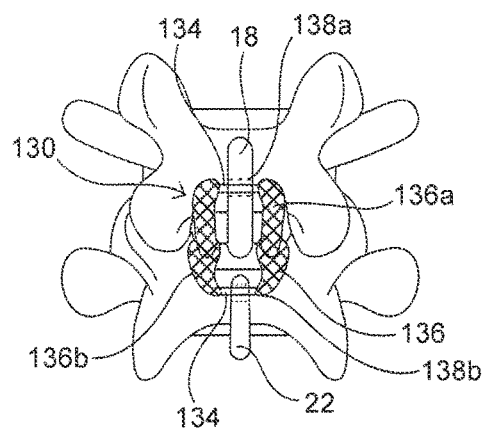
Figure 13C:
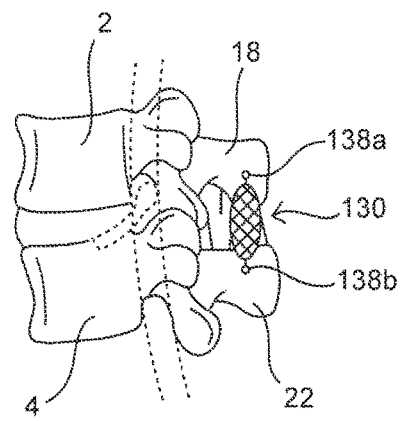
FIG. 13C is a side view of the posterior element distraction system of FIG. 13B.

FIGS. 13A-13C illustrate another posterior element distraction system 130 of the present invention having a two-piece configuration. System 130 includes superior component 132a and inferior component 132b which are similarly constructed, each having a transverse member 134 and lateral balloon members 136 at opposing ends. The difference between the two is in the profile or shape of the respective balloon members in an expanded configuration. In particular, balloons 136a of superior component 132a and balloons 138b are shaped to interlock with each other in a mating configuration so as to provide an anchor for transverse members 134. A punching tool 115 as described above may be used to create bores 138a and 138b, respectively, in spinous processes 18, 22. The superior and inferior components are independently delivered and implanted so that the transverse members 134 are positioned within the bores. Subsequently, all of the balloons 136 are inflated with superiorly and inferiorly opposing balloons 136a, 136b interconnecting in a mating configuration.

FIGS. 14A-14C, 15A-15C and 16A-16C each illustrate similar posterior element distraction systems having left and right lateral members, shown here in the form of expandable balloons. Each lateral member has a transverse member having a hook-like configuration for hooking around or about either a portion of the posterior element or a pedicle screw positioned within a portion of the posterior element.

Figure 14A:
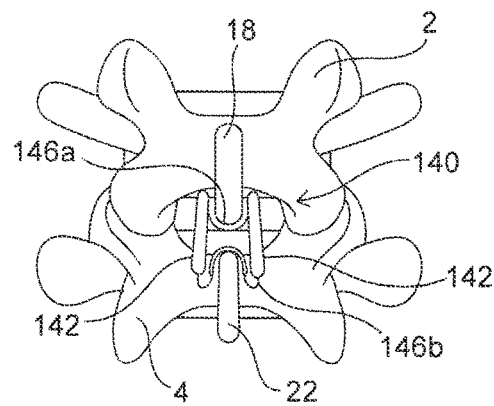
FIGS. 14A and 14B illustrate dorsal views of another bi-lateral posterior element distraction system of the present invention implanted within a spinal motion segment in unexpanded and expanded configurations, respectively.
Figure 14B:
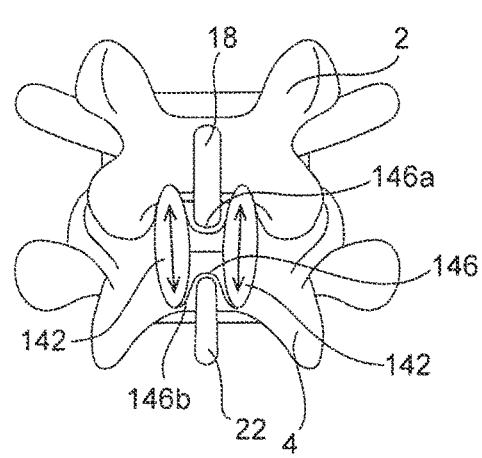
Figure 14C:
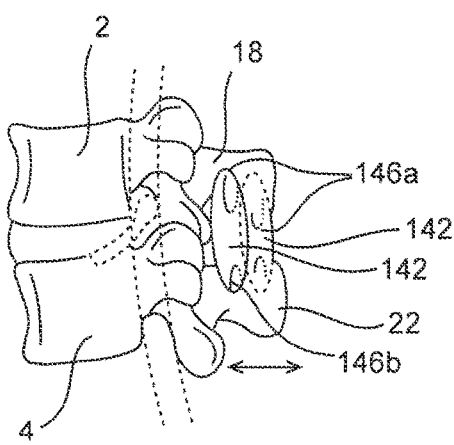
FIG. 14C is a side view of the posterior element distraction system of FIG. 14B.

For example, system 140 of FIGS. 14A-14C has hook-like transverse members 146, where each lateral balloon member 142 has a superior transverse hook 146a configured for hooking under the superior spinous process 18 and an inferior transverse hook 146*b* configured for hooking over the inferior spinous process 22. The hooks may be placed prior to inflation and, upon inflation of the lateral members 142, the respective hooks become securely anchored to the spinous processes. The pair of superior hooks 146*a* may be aligned to overlap or contact each other or to be displaced from each other as illustrated in FIG. 14C. The inferior hooks 146*a* may be similarly aligned.

Figure 15A:
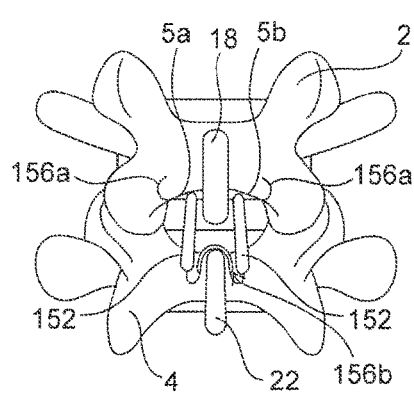
FIGS. 15A and 15B illustrate dorsal views of another bi-lateral posterior element distraction system of the present invention implanted within a spinal motion segment in unexpanded and expanded configurations, respectively.
Figure 15B:
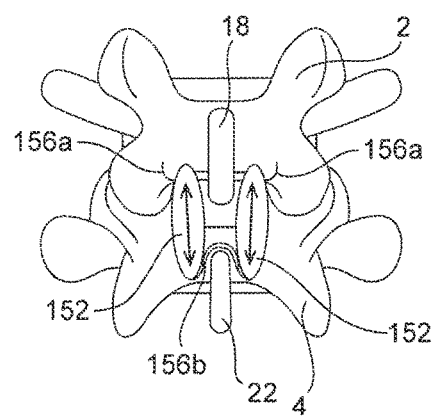
Figure 15C:
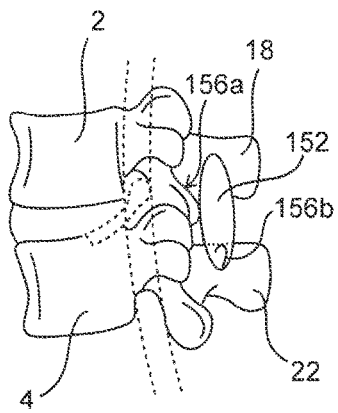
FIG. 15C is a side view of the posterior element distraction system of FIG. 15B.

System 150 of FIGS. 15A-15C has hook-like transverse members 156, where each lateral balloon member 152 has a superior transverse hook 156*a* configured for hooking under a respective laminal arch 5*a*, 5*b* and an inferior transverse book 156 configured for hooking over the inferior spinous process 22 as described above. The hooks may be placed prior to inflation of the lateral members 152 and, upon inflation of lateral members 152, the respective superior hooks 156*a* become securely anchored to respective portions of the laminal arch 5*a*, 5*b* of the superior vertebra 2, and the respective inferior hooks 156*b* engage with and securely anchor to the inferior spinous process 22.

System 160 of FIGS. 16A-16C has superior hook-like transverse members 166*a* where each lateral balloon member 162 is configured to hook about the pedicle screws 168. Here, pedicle screws 168 are positioned in the inferior facet joints 10*a*, 10*b*, respectively, and their supporting pedicles of superior vertebra 2. System 160 further includes inferiorly positioned 166*b* configured for hooking over the inferior spinous process 22 as described above. Prior to inflation of lateral members 162, the respective superior hooks 166*a* may be engage with or positioned about or secured by pedicle screws 168. Upon inflation of lateral members 162, the respective inferior hooks 166*b* securely anchor to the inferior spinous process 22.

Figure 17A:
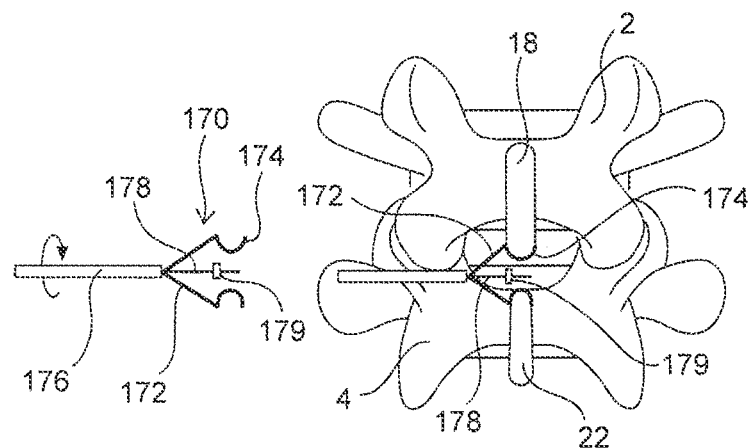
FIGS. 17A and 17B illustrate dorsal views of another hi-lateral posterior element distraction system of the present invention implanted within a spinal motion segment in unexpanded and expanded configurations, respectively.
Figure 17B:
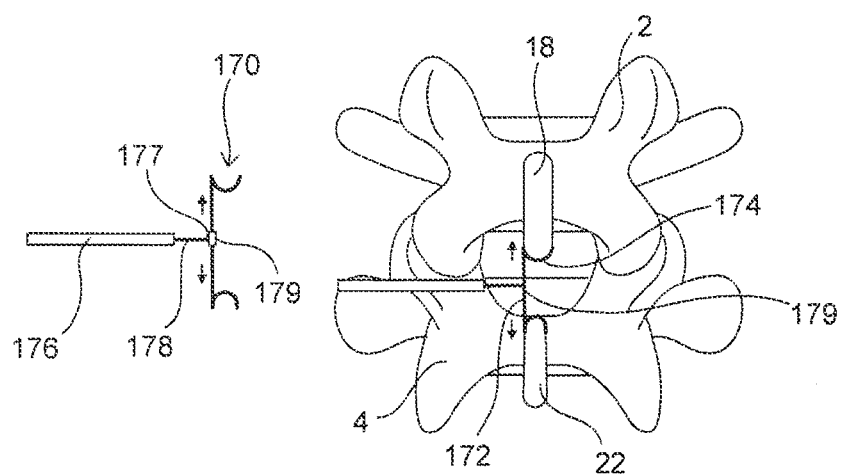

FIGS. 17A and 17B illustrate a unilateral posterior element distraction system 170 of the present invention. System 170 includes a single lateral member 172 which is in the form of an expandable strut having a hinged jaw configuration whereby the strut is foldable at a central joint 177, as shown in FIG. 17A. Hooked transverse members 174 are positioned at superior and inferior ends of strut 172 and are configured for engaging the underside of superior spinous process 18 and the top side of inferior spinous process 22. Transverse members 174 are preferably made from a superelastic material wherein they have a preformed hook configuration but are sufficiently flexible to be compressed to a straightened configuration. A working channel or delivery lumen 178 in conjunction with a pusher/guide wire 178 extendable and slidable through hinge joint 177 may used to deliver system 170 minimally invasively to the implant site whereby strut 172 is delivered in a folded condition and transverse members 174 are delivered in a straightened condition. Upon placement of the distal end of working channel 176 within the interspinous space, lumen 178 is retracted thereby releasing strut 172 whereby strut 172 straightens and transverse members 174 engage with the spinous processes 18, 22. To lock hinge joint 177 and maintain distraction of the vertebrae, wire 178 is retracted until its distal end, which terminates in a stop 179, is cause to abut hinge joint 177, as shown in FIG. 17B.

Figure 18A:
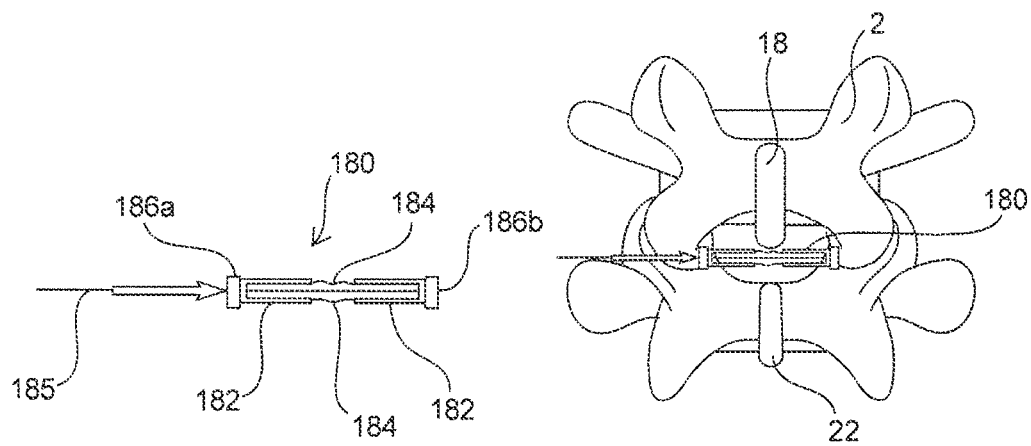
FIGS. 18A and 18B illustrate dorsal views of another bi-lateral posterior element distraction system of the present invention implanted within a spinal motion segment in unexpanded and expanded configurations, respectively.
Figure 18B:
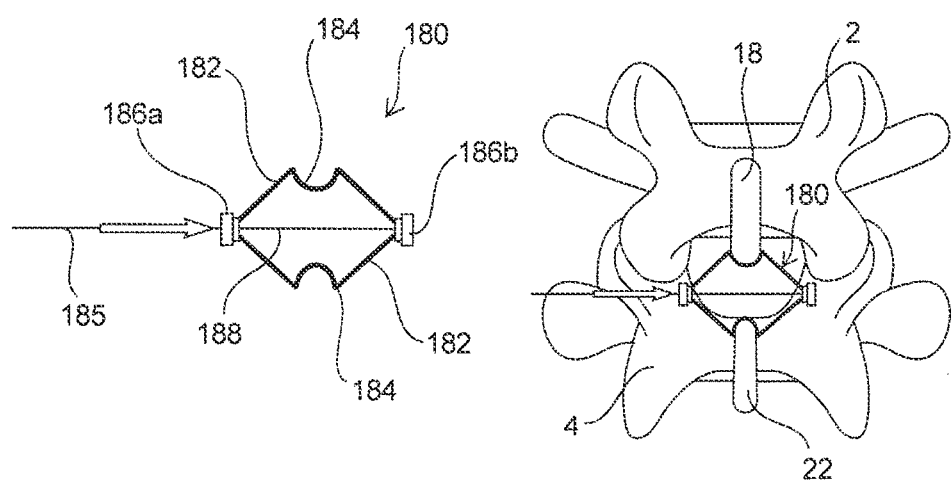

FIGS. 18A-18B illustrate another bi-lateral posterior element distraction system 180 having left and right lateral members 182, shown here in the form of compressible-expandable struts. Extending between the ends of struts 182 are transverse superior and inferior transverse members 184 which are preferably made from a superelastic material wherein they have a preformed curved configuration (FIG. 188) but are sufficiently flexible to be compressed to a straightened configuration (FIG. 18A). Each strut member 182 is hinged centrally at a hub 186 wherein the strut ends are foldable at hub 186. Extending between hubs 186 is a central transverse member 188. A guide wire 185 is threadably engaged with and extends proximally of hub 186*a*.

During delivery, the lateral and transverse members of system 180 are all in a compressed, low-profile state to be easily translated through a working channel to the interspinous space, as illustrated in FIG. 18A. Upon positioning within the space, the working channel (not shown) is withdrawn proximally. Guide wire 185 is then used to push against proximal hub 186*a* thereby expanding struts 182 and allowing transverse members 184 to achieve there expanded and curved configuration for engagement with the spinous processes 18, 22, as shown in FIG. 18B. Once the desired amount of distraction is achieved between vertebrae 2 and 4, guide wire 185 is unscrewed from proximal hub 186*a* thereby leaving system 180 at the implant site. Lateral struts 182 are sufficiently rigid to maintain the expanded condition and withstand the natural forces exerted on it by spine.

Figure 19A:
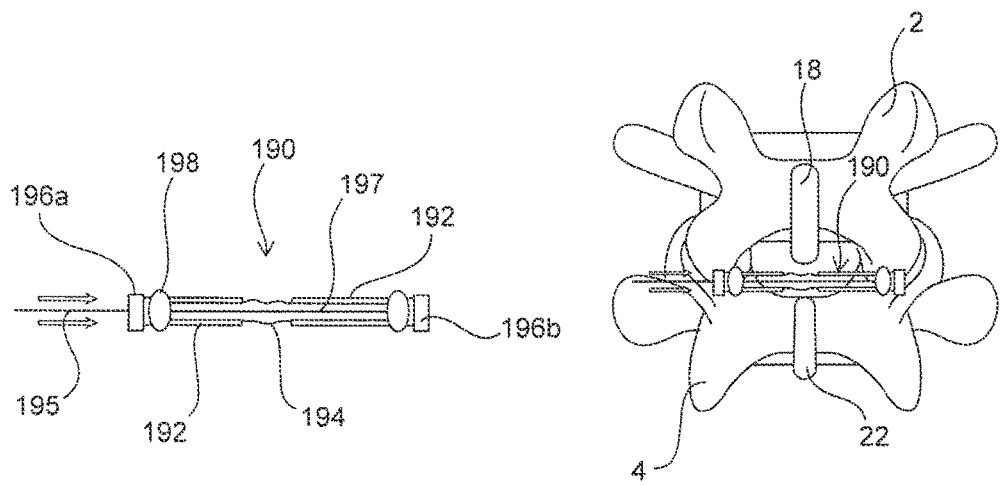
FIGS. 19A and 19B illustrate dorsal views of another bi-lateral posterior element distraction system of the present invention implanted within a spinal motion segment in unexpanded and expanded configurations, respectively.
Figure 19B:
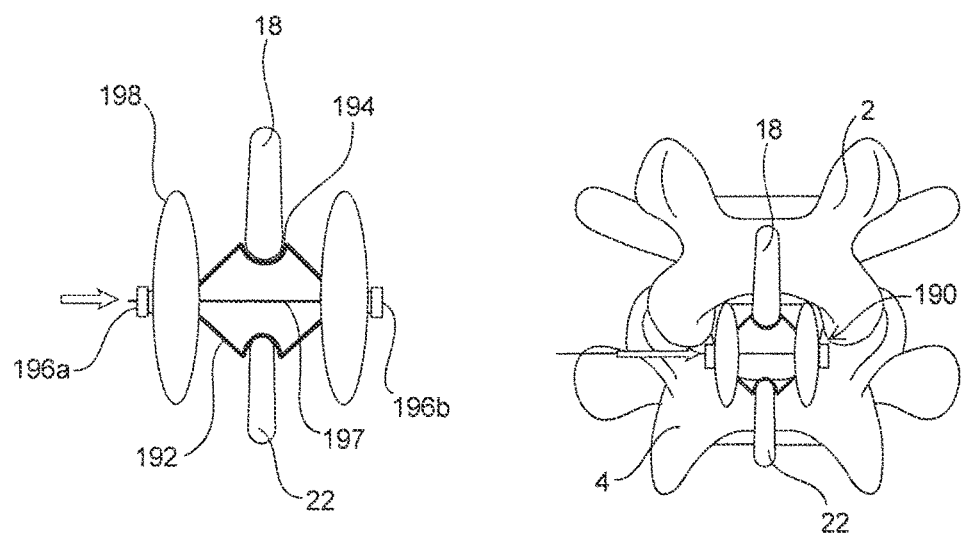

System 190 of FIGS. 19A and 19B is similar to the system of FIGS. 18A and 18B as just described in that expandable-compressible strut 192, preformed transverse members 194 and hubs 196 are substantially identical in structure and function. System 190, however, in that the lateral members further include expandable balloon members 198 positioned between hubs 198 and the exterior ends of struts 192, respectively. Additionally, central transverse member 197 provides a lumen by which balloon members 198 are in fluid communication with each other as well as with guide wire 195 which transports an inflation medium to the balloons. The delivery of system 190 to the implantation site is also similar to that described above with respect to the system of FIGS. 18A and 18B, with the additional step of inflating balloons 198, which may be done either prior to or after expanding strut members 192 within the interspinous space. Once the desired amount of vertebral distraction and balloon inflation is achieved, proximal hub 196*a* is locked in place and guide wire 195 is cut and removed. As such, balloons 198 function, at least in part, as anchors for and provide further stability to system 190.

The posterior element distraction systems of FIGS. 20-23 all provide lateral members, either in a unilateral or a bilateral arrangement, which have strut configurations, particularly wire forms which are configured to be spring-loaded wherein they are self-expandable from a compressed or retained condition. Moreover, the lateral struts have configurations which provide a substantially central "living hinge" about which the strut ends may be folded. Alternatively, the struts may be compressed along their length to a lower profile configuration to make them easily deliverable through a narrow working channel. The spring force provided by the struts is sufficient to create the desired distraction between the vertebrae 2, 4.

Figure 20A:
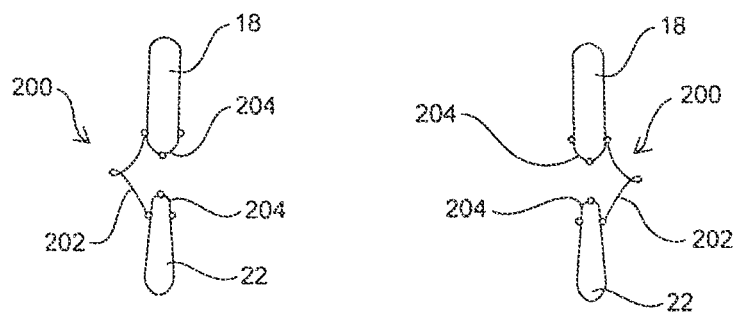
FIG. 20A illustrates two unilateral posterior element distraction systems of the present invention implanted in tandem within a spinal motion segment.
Figure 20B:
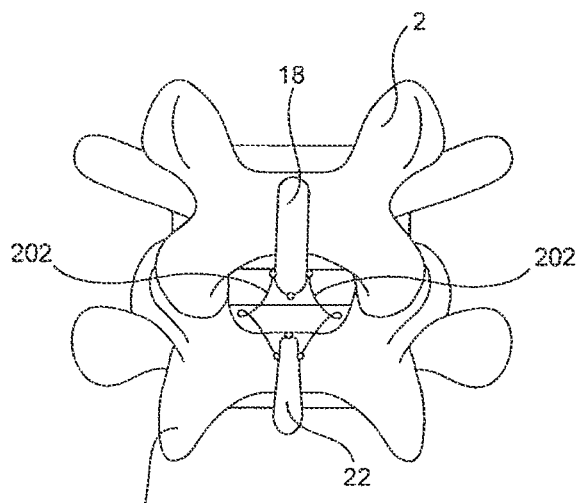
FIGS. 20B and 20C illustrate dorsal views of the tandem implant of FIG. 20A in unexpanded and expanded configurations, respectively.
Figure 20C:
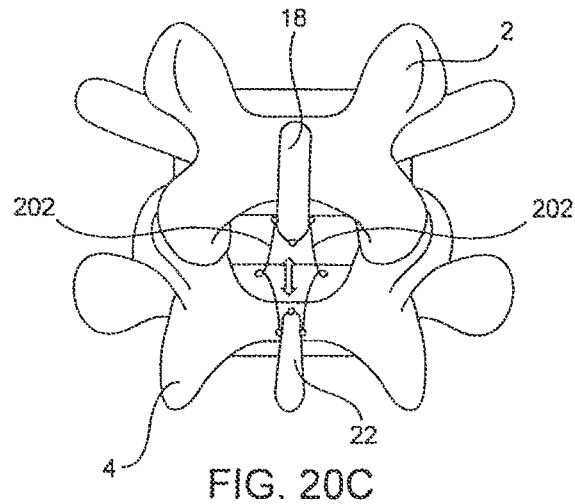

FIGS. 20A-20C illustrate a system 200 which is a unilateral system having a single lateral strut member 202. Transverse members 204, also of a wire form which may be substantially flexible so as to be straightenable during delivery through a working channel extend from the ends of strut member 202. While system 200 may be used alone, two systems 200 may be employed in tandem on opposite sides of an interspinous space, as illustrated in FIGS. 20B and 20C, depending on the clinical application at hand. The two systems may be delivered independently through separate incisions formed on both sides of the spine. Alternatively, the two systems may be delivered serially through the same incision and through the same working channel wherein the position of the systems within the working channel and upon delivery are opposite each other. In other words, the most distal of the two systems, and thus the first to be delivered, would be delivered hinge first while the more proximally positioned system would be delivered second with its transverse members leading through the working channel. Alternatively, the two may be delivered in the same or any suitable position and their positions subsequently manipulated once at the implant site.

Figure 21A:
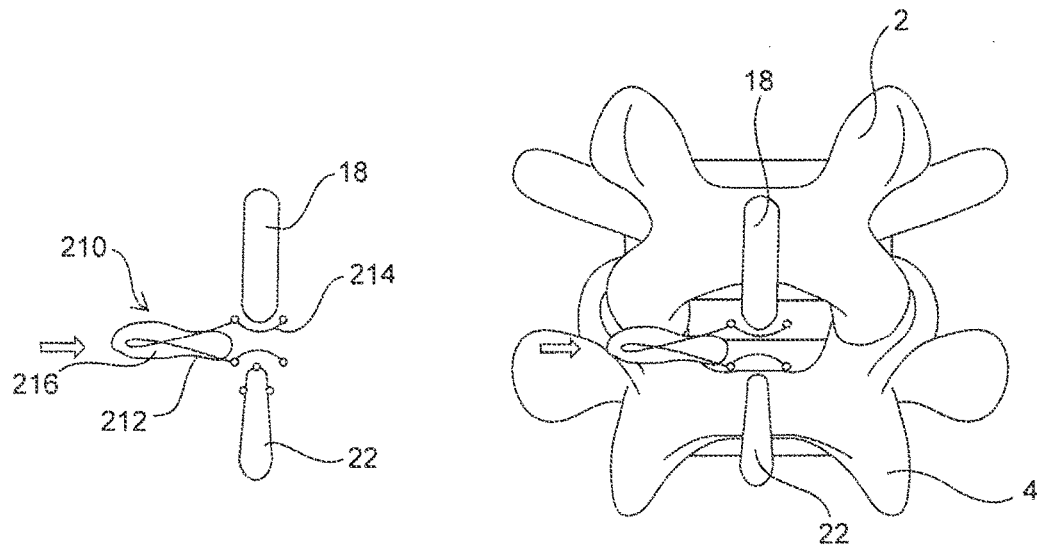
FIGS. 21A and 21B illustrate dorsal views of another unilateral posterior element distraction system of the present invention implanted within a spinal motion segment in unexpanded and expanded configurations, respectively.
Figure 21B:
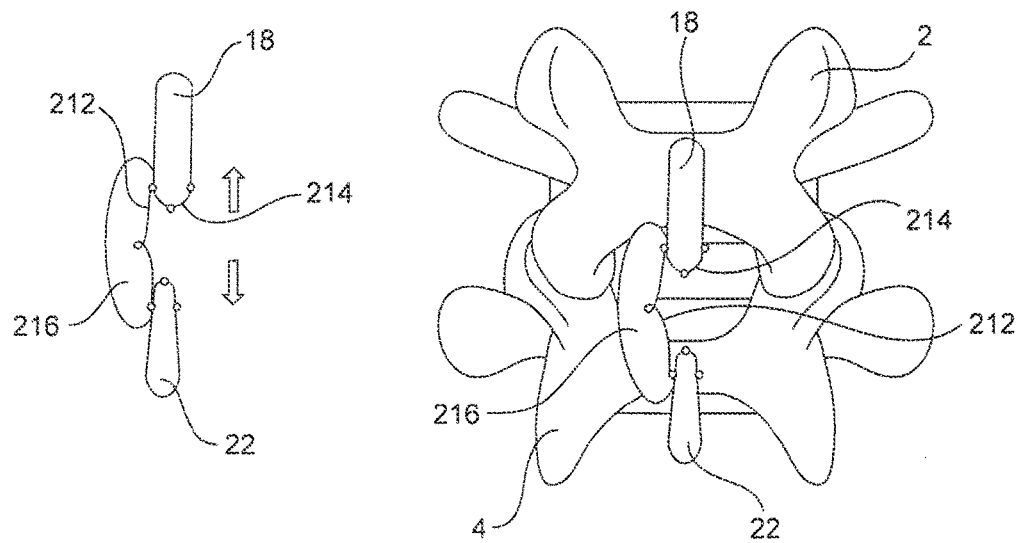

FIGS. 21A and 21B illustrate another unilateral system 210 similar to that of FIGS. 20A-20C, having a lateral strut member 212 and two transverse members 214. System 210, however, has an additional balloon member 216 attached along the length of strut member 212 which, upon expansion within the implant site provides additional stability and anchoring for system 210. Balloon member 216 is inflatable in the ways described above.

Figure 22A:
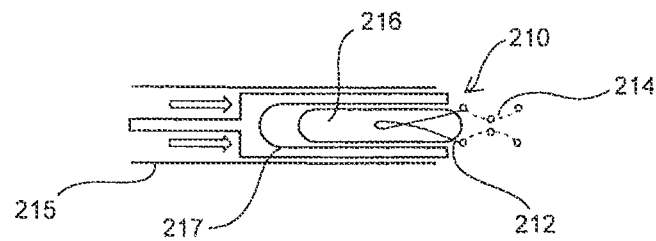
FIG. 22A illustrate the unilateral posterior element distraction system of FIGS. 21A and 21B within a delivery system of the present invention.
Figure 22B:
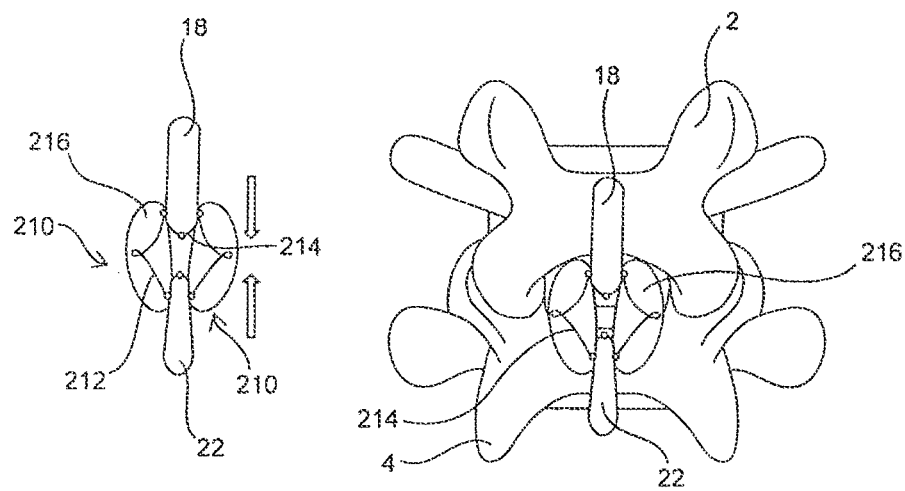
FIGS. 22B and 22C illustrate a dorsal views of the systems implanted in tandem within a spinal motion segment in various states of expansion.
Figure 22C:
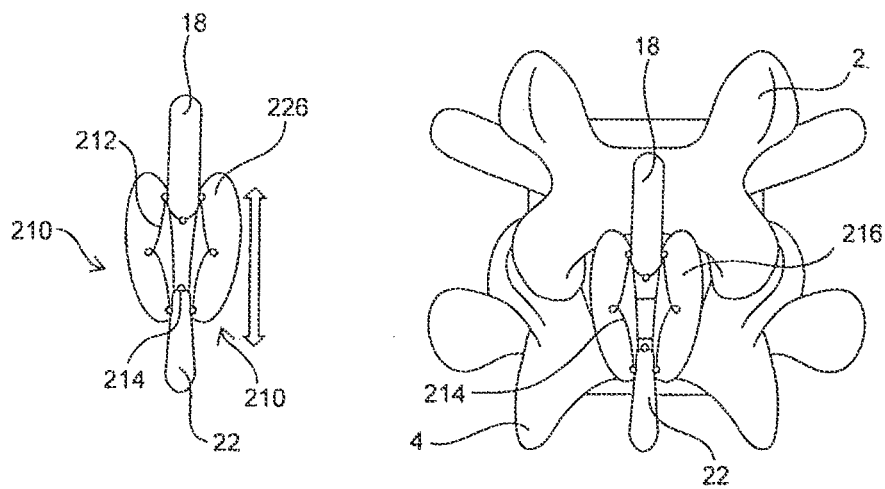

As with the unilateral system of FIGS. 20A and 20B, two of system 210 may be used in tandem on opposite sides of the spinal motion segment being treated. This arrangement is illustrated in FIGS. 22A-22C. FIG. 22A, however, illustrates another manner of delivering system 210, namely, delivering the system with balloon member 216 either partially or completely pre-inflated, i.e., prior to placement at the implant site. A cannula or working channel 215 is provided with a pusher mechanism 217 having a distal working end having a cylindrical cavity therein for holding system 210 with balloon 216 in an inflated state. Strut member 212 and transverse members 214, however, are still delivered in a compressed or low profile state. As such, pre-inflated balloon 216 facilitates the spring-loading of system 210 such that upon release of balloon 216 from the distal end of delivery means 217, system 210 may immediately expand. If additional distraction of the spinal motion segment is required, balloon 216 may be additionally inflated as needed.

Where a bilateral approach is used, both sides of the above-described unilateral system 210 may be integrally attached prior to implantation, thereby providing a bilateral system. Where the balloon members 216 are inflated subsequent to placement at the implant site, a lumen extending between the two may be provided so as to allow inflation of both balloons from one side. Alternatively, each of the balloons may have its own inflation port whereby they are inflated or expanded independently of each other. The inflation procedure may then be done bi-laterally or from the same inflation lumen.

Figure 23A:
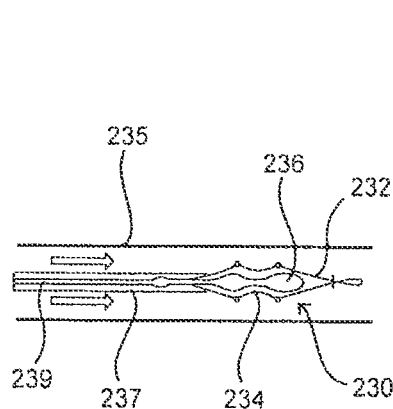
FIG. 23A illustrates another bi-lateral posterior element distraction system of the present invention in combination with a temporary distraction mechanism.
Figure 23B:
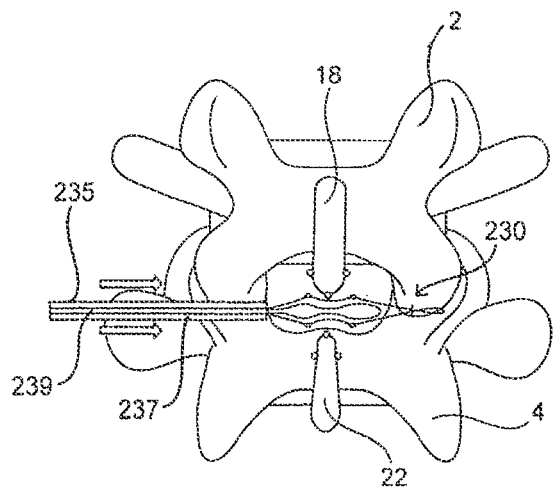
FIGS. 23B and 23C illustrate delivery of the distraction system and use of the temporary distraction mechanism to distract a spinal motion segment.
Figure 23C:
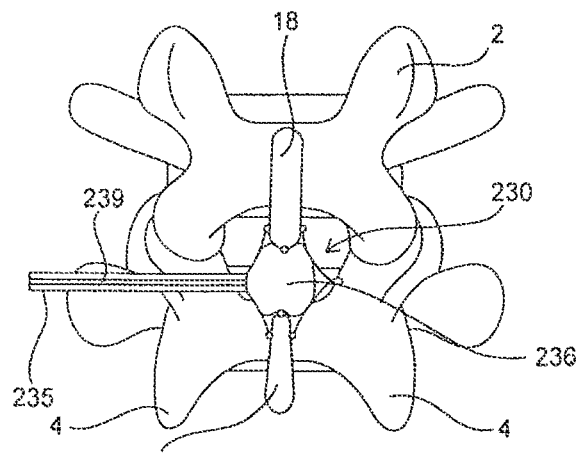
Figure 23D:
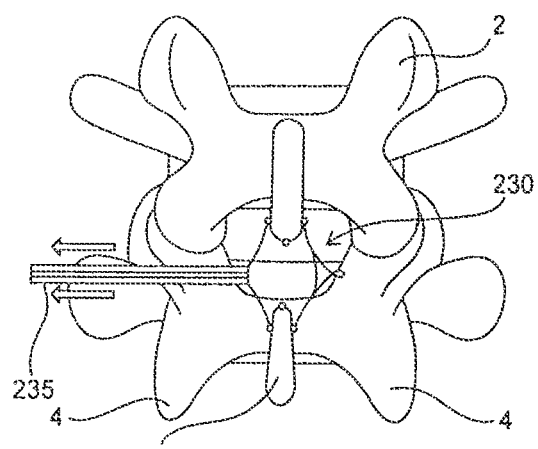
FIG. 23D illustrates the bi-lateral posterior element distraction system of FIG. 23A implanted within a spinal motion segment and subsequent to removing the distraction mechanism.

FIGS. 23A-23D illustrates a posterior distraction system 230 similar to that of FIGS. 20A-20C but having a bilateral configuration rather than a unilateral configuration. System 230 includes lateral members 232 and transverse members 234 which and is deliverable as described above. Here, however, the permanently implantable distraction system 230 is implanted with the use of a temporary distraction mechanism 226. Distraction mechanism 226 is in the form of an inflatable balloon which may be made of a compliant or non-compliant material. System 230 may be delivered in tandem with distraction mechanism 226 with the assistance of a pusher mechanism 237. As such, both are delivered through a single working channel 235 in a compressed or low profile state where system 230 is positioned over balloon 226. Alternatively, balloon 226 and system 230 may be delivered independently of each other through separate working channels or lumens whereby, when both are positioned within the interspinous space, they are staggered from each other anteriorly to posteriorly. As illustrated in FIG. 23B, both may be placed in the interspinous space simultaneously or distraction mechanism 226 may be initially placed while retaining system 230 within working channel 235. In either case, distraction member 236 is inflated via an inflation lumen 239 of pusher mechanism 237. As balloon 236 is inflated, vertebrae 2 and 4 are distracted relative to each other and system 230 is allowed to expand within the interspinous space. After the desire distraction is achieved, balloon 236 is deflated and removed from the implant site, as illustrated in FIG. 23D.

Figures 24A, 24B:
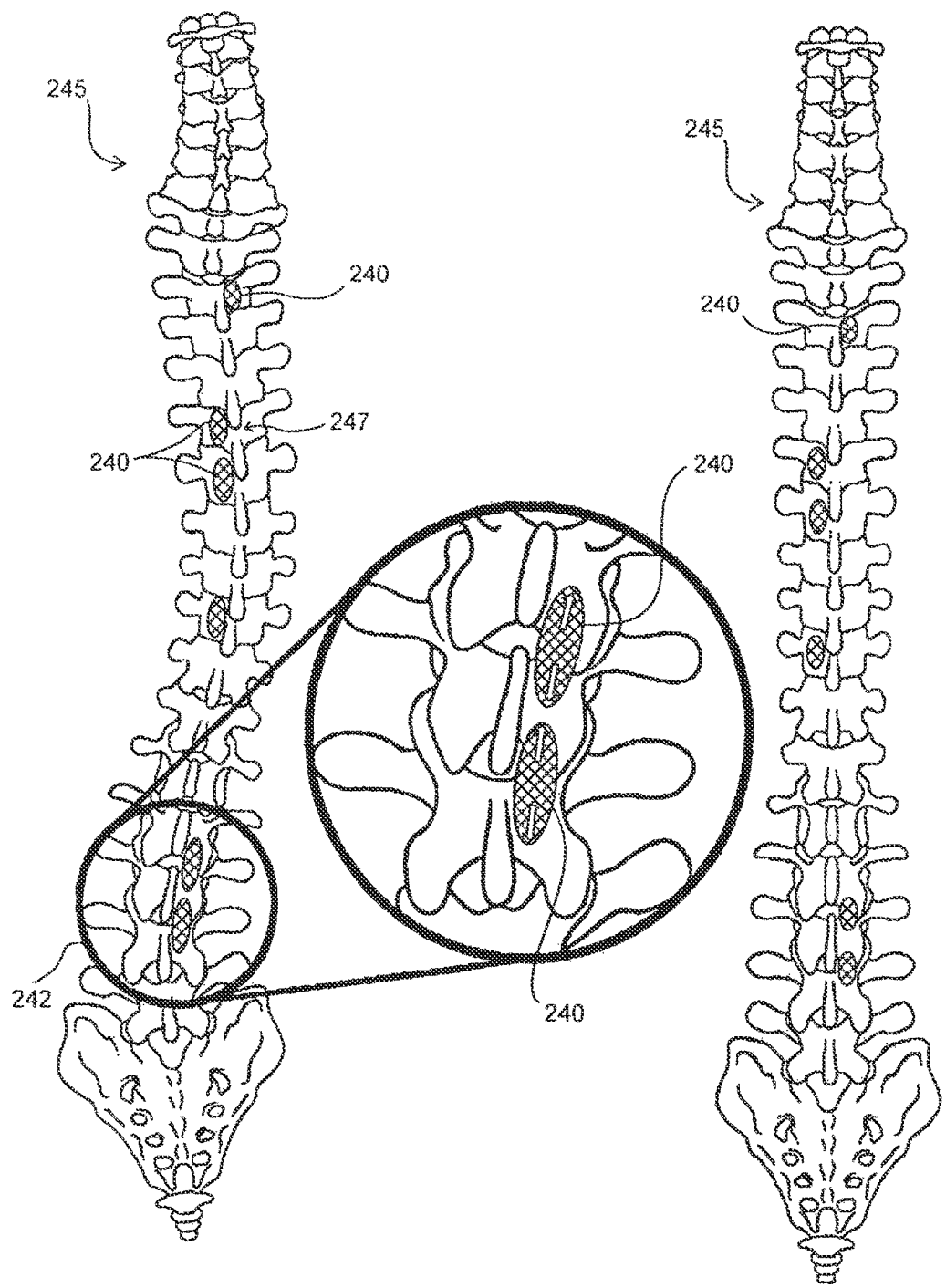
FIG. 24A illustrates a scoliotic spine having a plurality of unilateral posterior element distraction systems of the present invention implanted therein.
FIG. 24B illustrates the same spine after successful treatment utilizing the unilateral posterior element distraction systems.

FIGS. 24A and 24B illustrate use of a plurality of another unilateral posterior distraction devices 240 implanted within spine 245. Device 240 is in the form of an expandable balloon configured for positioning laterally of a spinal motion segment, and particularly laterally, on either side, of an interspinous space 247. Device 240 is particularly suitable for treating scoliosis where one or more devices are placed axially on one or both sides of spine 245. For example, curvature 242 of the spine, as illustrated in FIG. 24A, is treated by implanting one or more, e.g., two, on the concave side (here, the right side) of the spine adjacent the affected spinal motion segments. The devices are selectively expanded to rotationally distract the vertebrae of the affected segments such that the axial position of the spine is corrected, as illustrated in FIG. 24B. The devices may be configured to anchor themselves such as by having a shape that minimizes migration or may be further secured by other means such as a biological adhesive, pins, screws, etc.

Figure 25A:
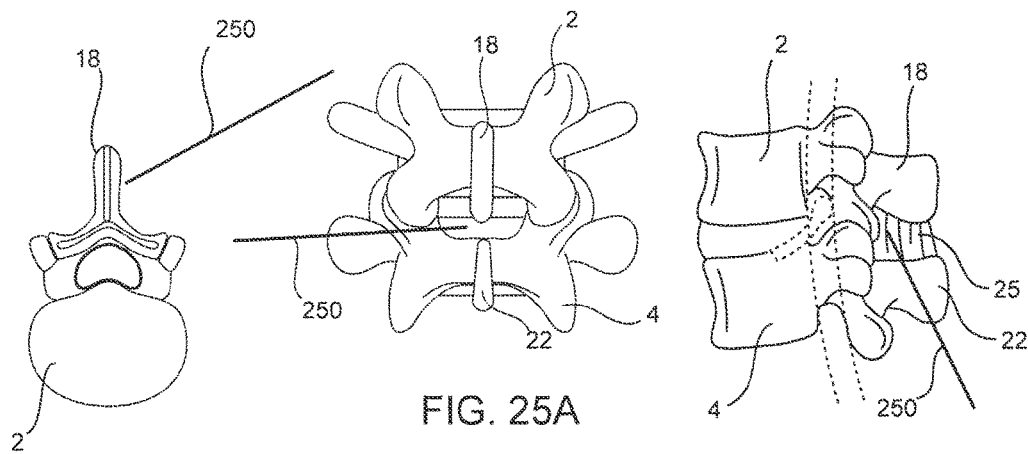
FIGS. 25A-25E illustrate the steps of a method of the present invention for percutaneously implanting certain systems of the present invention.
Figure 25B:
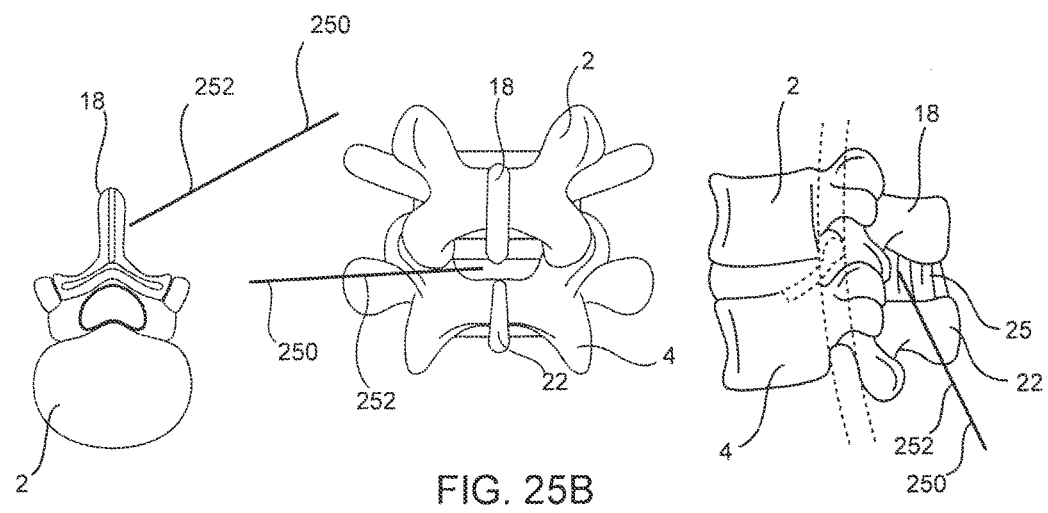
Figure 25C:
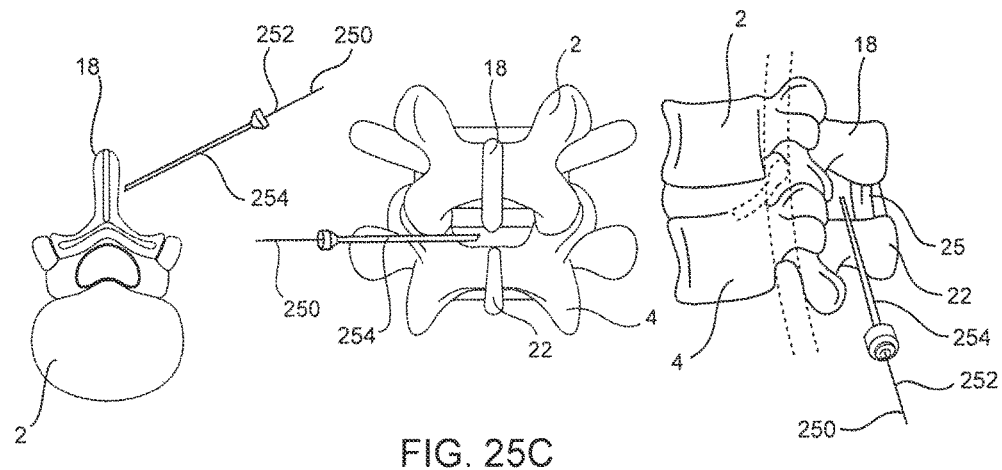
Figure 25D:
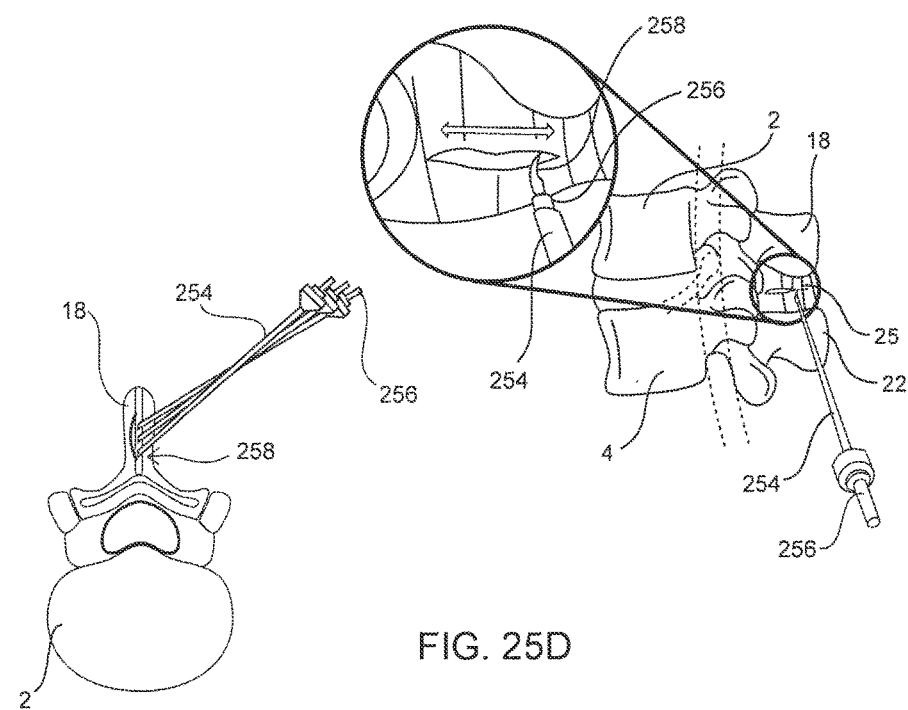
Figure 25E:
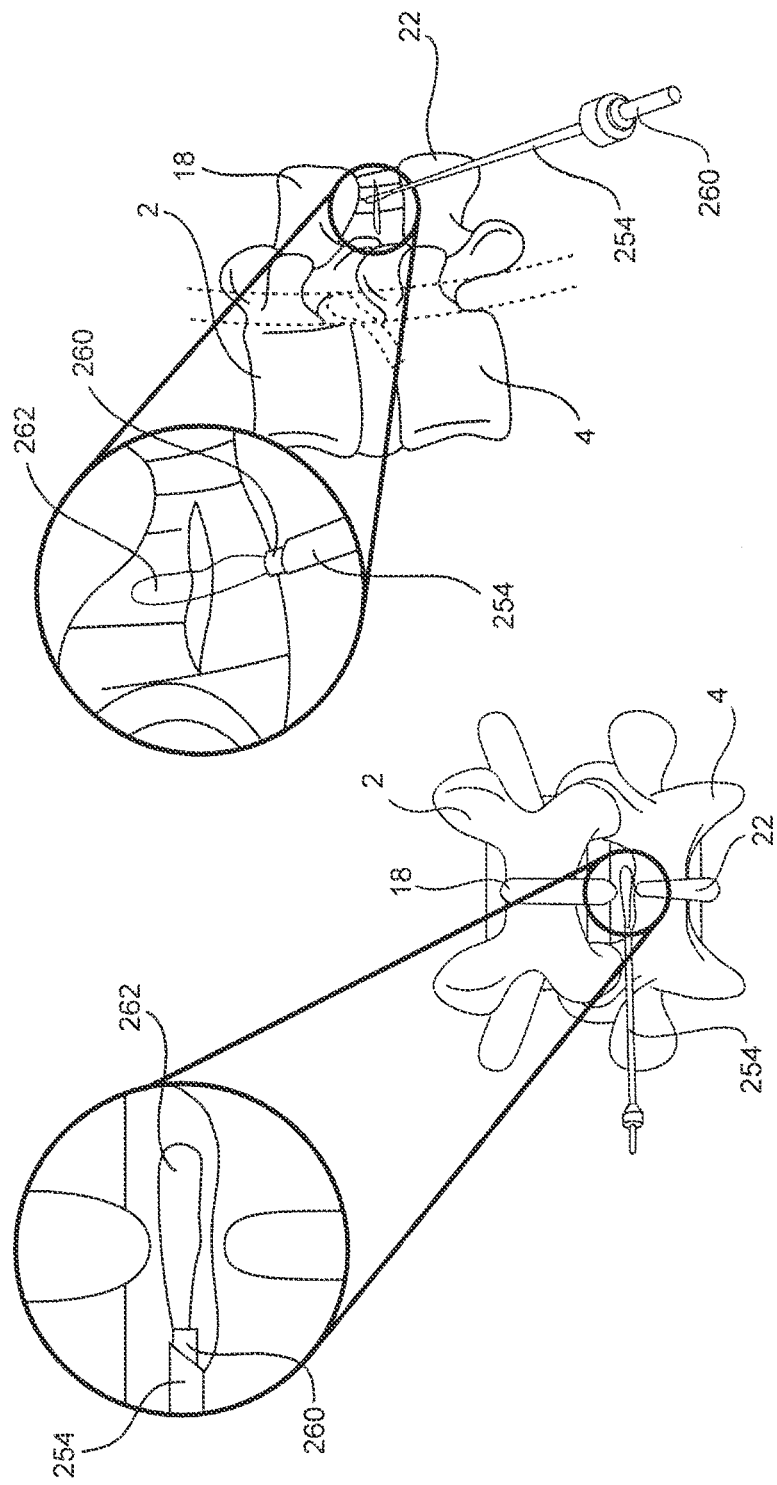

FIGS. 25A-25E illustrate certain preliminary steps of a minimally invasive procedure for implanting the devices and systems of the present invention. As illustrated in FIG. 25A, a percutaneous penetration or puncture is first made to one side of the spinal motion segment being treated. An instrument 250 commonly referred to as a "K-wire" may used to form the penetration. The instrument 250 may be directed under fluoroscopy or x-ray proximate a target implant site, such as between the vertebrae 2, 4 of the spinal motion segment being treated. As illustrated in FIG. 25B, a dilator 252 is then translated over k-wire 250 to within the target area to enlarge the channel through the tissue created by the k-wire. Then, as illustrated in FIG. 25C, a cannula or working channel 254 is translated over dilator 252 to within the target area to further expand the channel within the tissue and to provide a channel through which dissection, visualization and/or implantation instruments can be delivered. At this juncture in the procedure, k-wire 250 and dilator 252 may be removed from the implant site. A dissection tool 256, such as a scalpel 258, is then delivered through the lumen of working channel 254, and working channel 253 and is manipulated to allow dissection or incising of an area within or adjacent the implant site, e.g., the intraspinous ligament 25, as illustrated in FIG. 25D. Finally, as illustrated in FIG. 25E, a delivery or pusher instrument or lumen 260 within which a system 262 of the present invention is retained in an undeployed or partially undeployed state is translated through working channel 254 to the target implant site. The system or device 262 is then deployed and expanded or allowed to expand to an extent sufficient to distract vertebrae 2 and 4 or a portion of their posterior elements a desired amount.

In certain embodiments of present invention, either during the implant procedure or in a subsequent procedure, the size or volume of the implanted system may be selectively adjusted or varied. For example, after an initial assessment upon implant, it may be necessary to adjust, either reduce or increase, the size or volume of the spacer to optimize the intended treatment. Further, it may be intended to only temporarily implant the spacer for the purpose of treating a temporary condition, e.g., an injured or bulging or herniated disk, or scoliotic curvature. Once the repair is achieved or the treatment completed, the spacer may be removed, either with or without substantially reducing the size or volume of the spacer. In other embodiments, the implant as well as the inflation/expansion material, if one is used, may be made of biodegradable materials wherein the implant degrades after a time in which the injury is healed or the treatment completed.

For those implants of the present invention having a balloon configuration, the balloon may come equipped with an inflation or injection port for coupling to a source of inflation or expansion material or medium. The port may consist of a one-way valve which is self-sealing upon release from an inflation mechanism or lumen. The port may be further configured to releasably engage from an inflation tube, where such engagement may be threaded or involve a releasable locking mechanism.

Depending upon the material used to fabricate the expandable members of the present invention, they may have a degree of stiffness in an unexpanded or deflated state such that they may maintain an elongated configuration so as to be directly insertable and pushable through a working channel. This may be the case where the expandable member is made of a is strut or mesh material. Alternatively, a pusher or small diameter rod may be inserted through an inflation port of a balloon type expandable member to keep the expandable member in an elongated state so as to prevent it from bunching within the working channel and to provide some rigidity to more effectively position the expandable body in the target implant site.

With embodiments in which the balloon members are initially inflated with air and then filled with a solid or fluid medium, the latter is preferably not delivered or injected into the interior of the expandable body until the position of the expandable body within the interspinous space has been verified and optimized. This is beneficial in situations where, upon inflation, it is found that the expandable body is misaligned within the interspinous space and requires repositioning. The balloon member may simply be deflated of air to the extent necessary and repositioned in a less inflated or deflated state. If necessary, for example where it is found that the maximum distraction provided by the implant is insufficient for the particular application at hand, the implant may be completely deflated or compressed or both and removed and replaced with a more suitably sized implant.

It should be noted that any of the implants of the present invention may be implanted with the assistance of any of the temporary distraction mechanism of the present invention.

It should also be noted that any of the above-described steps or procedures, including but not limited to cannulation of the target area, dissection of the spinous ligament, insertion of the subject implants within the target implant site, inflation and/or expansion of a temporary distraction means, inflation and/or expansion of the implant or a portion thereof and the adjustment or readjustment of the implant may be facilitated by way of a scope delivered through a lumen of the working channel. Alternatively, a second cannula or working channel delivered through another percutaneous penetration on the same or opposite side of the spine may be employed for use of an endoscope and any other instruments needed to facilitate the procedure.

The subject devices and systems may be provided in the form of a kit which includes at least one interspinous device of the present invention. A plurality of such devices may be provided where the devices have the same or varying sizes and shapes and are made of the same or varying materials.

The kits may further include instruments and tools for implanting the subject devices, including but not limited to, a cannula, a trocar, a scope, a device delivery/inflation/expansion lumen, a cutting instrument, a screw driver, etc., as well as a selection of screws or other devices for anchoring the spacer tabs to the spinous processes. The kits may also include a supply of an inflation and/or expansion medium. Instructions for implanting the subject systems and devices and for using the above-described instrumentation may also be provided with the kits.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A method for distracting at least a portion of a subject's spinal motion segment comprising a superior vertebra, an inferior vertebra, each vertebra comprising a posterior element comprising a spinous process, laminal portions and a set of facet joints, and further comprising an interspinous space between the spinous processes, the method comprising:

positioning an expandable distraction member between the superior vertebra and the inferior vertebra;

distracting the superior vertebra and the inferior vertebra relative to each other to enlarge the interspinous space, wherein the expandable distraction member extends superiorly along opposite sides of the spinous process of the superior vertebra and the expandable distraction member extends inferiorly along opposite sides of the spinous process of the inferior vertebra;

after distracting the superior vertebra and the inferior vertebra, inserting an implantable expandable member, which has contact regions, through a cannula dimensioned to be positioned directly between adjacent spinous processes and into the enlarged interspinous space; and expanding the implantable expandable member such that the contact regions move away from one another, along the subject's sagittal plane, and into contact with the adjacent spinous processes and the expanded implantable expandable member maintains the distraction.

2. The method of claim 1, wherein the expandable distraction member is removed subsequent to the expanding of the implantable expandable member.

3. The method of claim 1, further comprising:

inserting a penetration instrument into a subject;

moving a dilator over the penetration instrument to define a channel in the subject;
moving the cannula over the dilator to expand the channel; and
moving the implantable expandable member along the channel and to the interspinous space.

4. The method of claim 1, further comprising:
moving the cannula toward the spinal motion segment to provide access to target tissue;
delivering a dissection instrument, a visualization instrument, and/or an implantation instrument through the cannula; and
manipulating tissue at a treatment site using the dissection instrument, the visualization instrument, and/or the implantation instrument positioned in the cannula.

5. The method of claim 1, further comprising:
before inserting the implantable expandable member, dissecting a ligament along the spinal motion segment to provide access to a target implantation site for the implantable expandable member.

6. The method of claim 1, further comprising:
moving a penetration instrument into a subject and toward the spinal motion segment;
moving a dilator over the penetration instrument to define a channel;
moving the cannula over the dilator to expand the channel; and
moving the implantable expandable member along the channel to position the implantable expandable member at the interspinous space before expansion of the implantable expandable member.

7. The method of claim 1, further comprising delivering the implantable expandable member through a cannula positioned in the subject, and
wherein the expandable distraction member and the implantable expandable member contact different regions of the superior vertebra and different regions of the inferior vertebra when the implantable expandable member contact moves into contact with the adjacent spinous processes.

8. A method for treating a subject, comprising:
moving a penetration instrument into the subject;
moving a dilator over the penetration instrument to define a channel in the subject's tissue;
moving a cannula over the dilator to expand the channel;
distracting adjacent spinous processes;
while the adjacent spinous processes are distracted,
moving an implantable device through a distal end of the cannula aligned with the interspinous space, wherein the distal end of the cannula is configured to fit between the adjacent spinous processes; and
deploying the implantable device connected to a delivery instrument positioned in the cannula such that portions of the deployed implantable device positioned within the interspinous space and along the subject's sagittal plane move away from one another to distract and/or maintain spacing between the adjacent spinous processes; and
holding first regions of the adjacent spinous processes to distract the adjacent spinous processes and inhibit lateral movement relatively to one another while deploying the implantable device,
wherein the deployed implantable device contacts second regions of the adjacent spinous processes that are different from the first regions.

9. The method of claim 8, further comprising:
inserting the implantable device between the distracted adjacent spinous processes such that the implantable device further distracts the adjacent spinous processes.

10. The method of claim 8, further comprising:
removing the dilator from the cannula before moving the implantable device through the cannula.

11. The method of claim 8, further comprising:
delivering a dissection instrument, a visualization instrument, and/or an implantation instrument through the cannula; and
manipulating tissue of the subject using the dissection instrument, the visualization instrument, and/or the implantation instrument positioned in the cannula.

12. The method of claim 8, wherein the penetration instrument is a wire.

13. The method of claim 8, wherein deploying the implantable device includes expanding the implantable device such that the implantable device distracts and/or stabilizes adjacent vertebrae.

14. The method of claim 8, further comprising:
releasing the implantable device from the delivery instrument; and
removing the delivery instrument from the cannula while the implantable device remains implanted between the adjacent spinous processes.

15. The method of claim 8, wherein a distal portion of the cannula positioned in the subject has a maximum cross-sectional dimension less than a distance between the adjacent spinous processes.

16. The method of claim 8, further comprising:
applying pressure to the adjacent spinous processes to enlarge an interspinous space therebetween, and
wherein the implantable device is deployed at the enlarged interspinous space.

* * * * *